US009782459B2

(12) United States Patent
Stephens, Jr. et al.

(10) Patent No.: US 9,782,459 B2
(45) Date of Patent: Oct. 10, 2017

(54) EOSINOPHIL PEROXIDASE COMPOSITIONS AND METHODS OF THEIR USE

(71) Applicant: Exoxemis, Inc., Little Rock, AR (US)

(72) Inventors: Jackson T. Stephens, Jr., Little Rock, AR (US); Matthew J. Pete, Elkhorn, NE (US)

(73) Assignee: EXOXEMIS, INC., Little Rock, AR (US)

( * ) Notice: Subject to any disclaimer, the term of this patent is extended or adjusted under 35 U.S.C. 154(b) by 61 days.

(21) Appl. No.: 14/150,619

(22) Filed: Jan. 8, 2014

(65) Prior Publication Data

US 2014/0120076 A1    May 1, 2014

Related U.S. Application Data

(63) Continuation of application No. PCT/US2012/046304, filed on Jul. 11, 2012.

(60) Provisional application No. 61/506,476, filed on Jul. 11, 2011.

(51) Int. Cl.
| | | |
|---|---|---|
| A61K 38/44 | (2006.01) | |
| A61K 45/06 | (2006.01) | |
| A61K 31/198 | (2006.01) | |
| A61K 31/327 | (2006.01) | |
| A61K 31/401 | (2006.01) | |
| A61K 33/40 | (2006.01) | |

(52) U.S. Cl.
CPC ............ *A61K 38/44* (2013.01); *A61K 31/198* (2013.01); *A61K 31/327* (2013.01); *A61K 31/401* (2013.01); *A61K 33/40* (2013.01); *A61K 38/443* (2013.01); *A61K 45/06* (2013.01); *C12Y 101/03004* (2013.01); *C12Y 111/01007* (2013.01)

(58) Field of Classification Search
CPC .... A61K 38/44; A61K 31/198; A61K 31/327; A61K 31/401; A61K 33/40; A61K 45/06; A61K 38/443; A61K 2300/00; C12Y 101/03004; C12Y 111/01007
See application file for complete search history.

(56) References Cited

U.S. PATENT DOCUMENTS

| | | | |
|---|---|---|---|
| 2,679,533 A | 5/1954 | Darragh | |
| 4,320,116 A | 3/1982 | Björck | |
| 4,473,550 A | 9/1984 | Rosenbaum | |
| 4,588,586 A | 5/1986 | Kessler | |
| 4,726,948 A | 2/1988 | Prieels | |
| 4,937,072 A | 6/1990 | Kessler | |
| 4,996,146 A | 2/1991 | Kessler | |
| 5,085,873 A | 2/1992 | Degre | |
| 5,206,156 A | 4/1993 | Samain | |
| 5,389,369 A | 2/1995 | Allen | |
| 5,451,402 A | 9/1995 | Allen | |
| 5,510,104 A | 4/1996 | Allen | |
| 5,565,197 A | 10/1996 | Allen | |
| 5,718,896 A | 2/1998 | Allen | |
| 5,756,090 A | 5/1998 | Allen | |
| 5,888,505 A | 3/1999 | Allen | |
| 6,033,662 A | 3/2000 | Allen | |
| 6,294,168 B1 | 9/2001 | Allen | |
| 6,503,507 B1 | 1/2003 | Allen | |
| 8,945,540 B2 | 2/2015 | Becquerelle et al. | |
| 2008/0114054 A1 | 5/2008 | Microbes et al. | |
| 2009/0280102 A1* | 11/2009 | Becquerelle | A61K 38/44 424/94.4 |

FOREIGN PATENT DOCUMENTS

| | | |
|---|---|---|
| EP | 0 307 376 A1 | 3/1989 |
| EP | 0 361 908 A2 | 4/1990 |
| EP | 0 514 417 B1 | 11/1992 |
| GB | 2 108 387 A | 5/1983 |
| WO | 88/02600 A1 | 4/1988 |

OTHER PUBLICATIONS

Gutierrez-Correa et al., Trypanosoma cruzi dihydrolipoamide dehydrogenase is inactivated by myeloperoxidase-generated "reactive species", Free Radic. Res., Jul. 2000, vol. 33, No. 1, pp. 13-22; attached Abstract Only—total p. 1.*
Kanofsky, et al., "Bromine derivatives of amino acids as intermediates in the peroxidase-catalyzed formation of singlet oxygen", Archives of Biochemistry and Biophysics, Academic Press, US, vol. 274, No. 1, Oct. 1, 1989, pp. 229-234.
European Search Report, EP12810678, dated Jan. 29, 2015, 8 pgs.
International Search Report, PCT/US2012/046304, dated Jan. 30, 2013, 7 pgs.
Anderson, M.M., et al., "The Myeloperoxidase System of Human Phagocytes Generates N?-(carboxymethyl)lysine on Proteins: a Mechanism for Producing Advanced Glycation End Prodicts at Sites of Inflammation," The Journal of Clinical Investigation 104(1):103-113, Jul. 1999.
Belding, M.E., and S.J. Klebanoff, "Peroxidase-Mediated Virucidal Systems," Science 167:195-196, Jan. 1970.
Clark, R.A., et al., "Peroxidase-H2O2-Halide System: Cytotoxic Effect on Mammalian Tumor Cells," Blood: The Journal of Hematology 45(2):161-170, Feb. 1975.
Hamon, C.B., and S.J. Klebanoff, "A Peroxidase-Mediated, *Streptococcus mitis*-Dependent Antimicrobial System in Saliva," Journal of Experimental Medicine 137:438-450, 1973.
Klebanoff, S.J., "Myeloperoxidase-Halide-Hydrogen Peroxide Antibacterial System," Journal of Bacteriology 95 (6):2131-2138, Jun. 1968.

(Continued)

*Primary Examiner* — Satyendra K Singh
(74) *Attorney, Agent, or Firm* — K&L Gates LLP

(57) ABSTRACT

Eosinophil peroxidase compositions and methods of their use for killing and/or inhibiting the growth of susceptible microorganisms are provided. The compositions include an eosinophil peroxidase, a peroxide or peroxide source, and amino acids glycine, L-alanine, and L-proline.

17 Claims, 10 Drawing Sheets

(56) References Cited

OTHER PUBLICATIONS

Klebanoff, S.J., "Myeloperoxidase-Mediated Antimicrobial Systems and Their Role in Leukocyte Function" (presented at the Symposium on Membrane Function and Electron Transfer to Oxygen, Miami, Jan. 22-24, 1969), in J. Schultz (ed), "Biochemistry of the Phagocytic Process," North-Holland Publishing Company, Netherlands, 1970, pp. 89-110.

Klebanoff, S.J., and C.C. Shepard, "Toxic Effect of the Peroxidase-Hydrogen Peroxide-Halide Antimicrobial System on Mycobacterium leprae," Infection and Immunity 44(2):534-536, May 1984.

Klebanoff, S.J., and M.E. Belding, "Virucidal Activity of H2O2-Generating Bacteria: Requirement for Peroxidase and a Halide," Journal of Infectious Diseases 129(3):345-348, Mar. 1974.

Klebanoff, S.J., et al., "Antimicrobial Activity of Myeloperoxidase," in L. Packer (ed.), "Methods in Enzymology," vol. 105, "Oxygen Radicals in Biological Systems," Academic Press, New York, 1984, pp. 399-403.

Klebanoff, S.J., et al., "The Peroxidase-Thiocyanate-Hydrogen Peroxide Antimicrobial System," Biochimica et Biophysica Acta 117(1):63-72, Mar. 1966.

Lehrer, R.I., "Antifungal Effects of Peroxidase Systems," Journal of Bacteriology 99(2):361-365, Aug. 1969.

Mickelson, M.N., "Effect of Lactoperoxidase and Thiocyanate on the Growth of *Streptococcus pyogenes* and *Streptococcus agalactiae* in a Chemically Defined Culture Medium," Journal of General Microbiology 43(1):31-43, Apr. 1966.

Moguilevsky, N., et al., "Lethal Oxidative Damage to Human Immunodeficiency Virus by Human Recombinant Myeloperoxidase," FEBS Letters 302(3):209-212, May 1992.

Rosen, H., and S.J. Klebanoff, "Formation of Singlet Oxygen by the Myeloperoxidase-Mediated Antimicrobial System," Journal of Biological Chemistry 252(14):4803-4810, Jul. 1977.

Steele, W.F., and M. Morrison, "Antistreptococcal Activity of Lactoperoxidase," Journal of Bacteriology 97 (2):635-639, Feb. 1969.

* cited by examiner

EOSINOPHIL PEROXIDASE COMPOSITIONS AND METHODS OF THEIR USE

CROSS-REFERENCE TO RELATED APPLICATION

This application is a continuation of International Application PCT/US2012/046304 having an international filing date of Jul. 11, 2012, which claims the benefit of U.S. Provisional Patent Application No. 61/506,476, filed Jul. 11, 2011, each application expressly incorporated herein by reference in its entirety.

BACKGROUND OF THE INVENTION

As disclosed in U.S. Pat. Nos. 5,888,505 and 6,294,168, eosinophil peroxidase may be used to selectively bind to and, in the presence of peroxide and halide, inhibit the growth of target microorganisms without eliminating desirable microorganisms or significantly damaging other components of the medium, such as host cells and normal flora, in the target microorganism's environment. Eosinophil peroxidase has previously been known to exhibit microorganism killing activity in natural systems when presented with an appropriate halide cofactor ($X^-$) and hydrogen peroxide as substrate (Klebanoff, 1968, *J. Bacteriol.* 95:2131-2138). However, the selective nature of eosinophil peroxidase binding and the utility of these systems for therapeutic, research and industrial applications has only recently been recognized. Due to the newly discovered selective binding properties of eosinophil peroxidase, when a target microorganism, such as a pathogenic microorganism, has a binding capacity for eosinophil peroxidase greater than that of a desired microorganism, such as members of the normal flora, the target microorganism selectively binds the eosinophil peroxidase with little or no binding of the eosinophil peroxidase by the desired microorganism. In the presence of peroxide and halide, the target bound eosinophil peroxidase catalyzes halide oxidation and facilitates the disproportionation of peroxide to singlet molecular oxygen ($^1O_2$) at the surface of the target microorganism, resulting in selective killing of the target microorganism with a minimum of collateral damage to the desired microorganism or physiological medium. Thus, as disclosed in U.S. Pat. Nos. 5,888,505 and 6,294,168, eosinophil peroxidase can be employed as an antiseptic in the therapeutic or prophylactic treatment of human or animal subjects to selectively bind to and kill pathogenic microorganisms with a minimum of collateral damage to host cells and normal flora of the host.

The system may also be employed as disinfecting or sterilizing formulations for inhibiting the growth of target microorganisms in vitro, particularly in applications where biomedical devices, such as bandages, surgical instruments, suturing devices, catheters, dental appliances, contact lenses and the like, are antiseptically treated to inhibit the growth of target microorganisms without damage to host cells of a subject when the biomedical device is subsequently utilized in vivo.

As disclosed in U.S. Pat. Nos. 5,389,369 and 5,451,402, while the eosinophil peroxidase antiseptic system disclosed in U.S. Pat. Nos. 5,888,505 and 6,294,168 has been found to be highly effective in the treatment of pathogenic microbes, an antimicrobial activity enhancing agent may be required for the effective killing of yeast and spore forming microorganisms. The spore stage of the microbial life cycle is characterized by metabolic dormancy and resistance to environmental factors that would destroy the microbe in its vegetative stage. The earliest phase of spore germination is characterized by swelling and a shift from dormancy to active metabolism. Vegetative growth, e.g., sprouting, and ultimately reproduction follows.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine is reported to stimulate bacterial spore germination (Hills, 1950, *J Gen Microbiol* 4:38; Halvorson and Church, 1957, *Bacteriol Rev* 21:112). L-Alanine and L-proline have also been reported to initiate fungal spore germination (Yanagita, 1957, *Arch Mikrobiol* 26:329).

Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate which is the end product of glycolytic metabolism (Embden-Meyerhof-Parnas Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle) which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

Accordingly, U.S. Pat. Nos. 5,389,369 and 5,451,402 disclose that the microbiocidal action of eosinophil peroxidase against yeast and sporular forms of microbes may be enhanced by treating the microorganisms with eosinophil peroxidase in combination with certain α-amino acids which provide a stimulating effect on yeast budding, germination of sporulated microbes, and possibly acceleration of metabolism of vegetative microbes. Representative α-amino acids disclosed for this purpose include glycine and the L- or D-enantiomers of alanine, valine, leucine, isoleucine, serine, threonine, lysine, phenylalanine, tyrosine, and the alkyl esters thereof. While U.S. Pat. Nos. 5,389,369 and 5,451,402 disclose the enhancement of microbiocidal activity of eosinophil peroxidase against yeast and sporular forms of microbes with α-amino acids, these patents do not disclose enhancement of the eosinophil peroxidase microbiocidal system against non-sporular bacterial or the further enhancement of antibacterial activity by the use of eosinophil peroxidase and at least two amino acids, as disclosed herein.

SUMMARY OF THE INVENTION

The present invention provides eosinophil peroxidase compositions and methods for killing or inhibiting microbial infections, such as bacterial infections, using the compositions.

In one aspect of the invention, compositions for killing or inhibiting the growth of a susceptible microorganism are provided.

In one embodiment, the composition includes an eosinophil peroxidase (EPO); a peroxide or peroxide source; and at least two amino acids that enhance the composition's microbiocidal activity. In one embodiment, the peroxide is hydrogen peroxide. In one embodiment, the peroxide source is a peroxide-producing oxidase (e.g., glucose oxidase (GO)).

In another embodiment, the composition includes an eosinophil peroxidase, a peroxide-producing oxidase, and at least two amino acids that enhance the composition's microbiocidal activity.

Amino acids suitable for the compositions of the invention include glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, ethyl 3-aminobutyrate, sarcosine methyl ester hydrochloride and nipecotic acid, alkyl esters, pharmaceutically acceptable salts, and mixtures thereof. In one embodiment, the at least two amino acids are selected from glycine, L-alanine, L-proline, and mixtures thereof. In one embodiment, the at least two additional amino acids are glycine, L-alanine, and L-proline.

In one embodiment, the composition comprises an eosinophil peroxidase, a peroxide or peroxide source, and amino acids glycine, L-alanine, and L-proline.

In certain embodiments, the compositions further include a halide selected from the group consisting of chloride, bromide, and mixtures thereof. In one embodiment, the halide is bromide (e.g., NaBr, KBr).

In certain embodiments, the compositions of the invention include from about 0.1 to about 1,000 µg/mL of eosinophil peroxidase. In certain embodiments, the compositions of the invention include from about 0.1 to about 500 mM of each amino acid. For certain embodiments that include glucose oxidase, the compositions include from about 1 to about 500 U/ml of glucose oxidase.

In other aspects, the invention provides methods for using the compositions.

In one embodiment, the invention provides a method for killing or inhibiting the growth of a susceptible microorganism. In the method, the microorganism is contacted with an effective amount of a composition of the invention.

In another embodiment, the invention provides a method for treating an infection in a human or animal subject. In the method, an effective amount of a composition of the invention is administered to the site of infection.

In a further embodiment, the invention provides a method for treating or preventing infection of a surgical site in a human or animal subject. In the method, an effective amount of a composition of the invention is administered to the surgical site. Representative surgical sites that can be advantageously treated include cancer surgical sites (e.g., colorectal cancer surgical site, brain cancer surgical site) and laparoscopic surgical sites, among others.

In the above methods, polymicrobial infections and multidrug resistant infections can be advantageously treated.

In a further aspect of the invention, a binary combination is provided. In one embodiment, the combination includes a first composition comprising an eosinophil peroxidase composition of the invention and a second composition comprising a substrate for a peroxide-producing oxidase in an aqueous medium. In one embodiment of the combination, the peroxide-producing oxidase is glucose oxidase and the substrate is glucose.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION OF THE INVENTION

Figure 1:
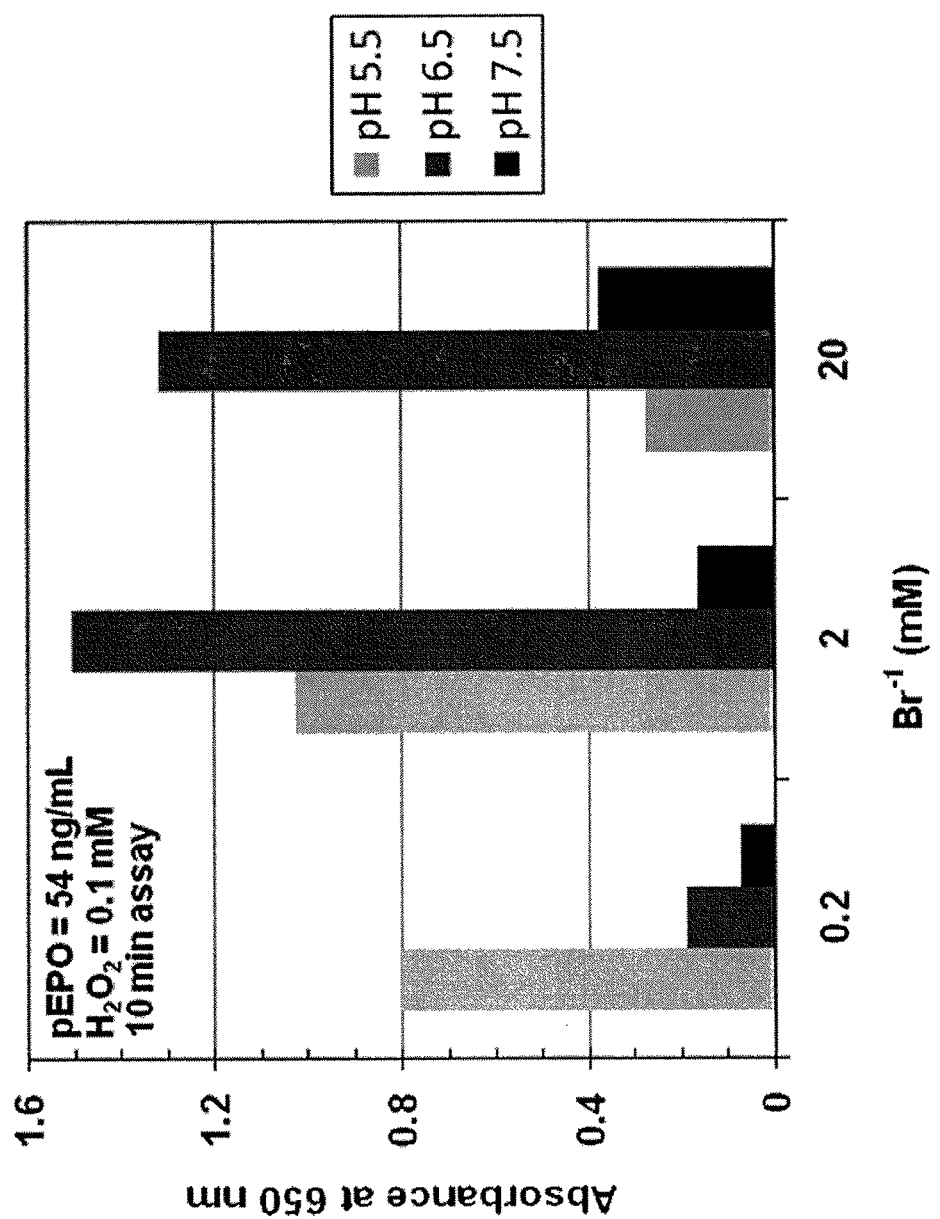
FIG. 1 is a graph comparing porcine eosinophil peroxidase (p-EPO) activity as a function of pH (5.5, 6.5, and 7.5) and bromide concentration (0.2, 2, 20 mM) in an in vitro assay quantitating N-bromotaurine by oxidation of 3,3',5,5'-dimethylbenzidine absorbance at 650 nm) (p-EPO 54 ng/mL, $H_2O_2$ 0.1 mM, 10 min assay).

The present invention is directed to compositions and methods for the killing or inhibition of bacterial infections using eosinophil peroxidase and at least two amino acids that work alone or in combination to enhance the microbiocidal activity of eosinophil peroxidase. In the practice of the invention, susceptible microorganisms are killed or inhibited by contacting the microorganisms with effective amounts of eosinophil peroxidase and at least two amino acids, in the presence of a peroxide and bromide or chloride, to inhibit the growth of or kill the microorganisms.

In one aspect of the invention, a composition for inhibiting the growth of a susceptible microorganism is provided. In one embodiment, the composition comprises an eosinophil peroxidase, a peroxide or peroxide source, and at least two amino acids. In one embodiment, the composition comprises an eosinophil peroxidase, a peroxide or peroxide source, and amino acids glycine, L-alanine, and L-proline. The amino acids in combination enhance the composition's microbiocidal activity. As used herein, the term "susceptible microorganism" refers to a microorganism that is advantageously killed or whose growth is inhibited by the eosinophil peroxidase compositions of the invention. Representative susceptible microorganisms are described below and in Examples 2-4.

In one embodiment, the peroxide is hydrogen peroxide. Other suitable peroxides are described below.

In another embodiment, the composition includes a peroxide source. Representative peroxide sources include peroxide-producing oxidases. Suitable peroxide sources and peroxide-producing oxidases are described below. In general, the peroxide-producing oxidase is present in an amount effective to generate from 100 pmol to 50 µmol peroxide per ml per minute in the presence of a substrate for the oxidase. In one embodiment, the peroxide-producing oxidase is glucose oxidase. For this embodiment, the substrate is glucose. In certain embodiments, the composition includes from about 1 to about 500 U/ml of glucose oxidase.

To enhance the eosinophil peroxidase's microbiocidal activity, the compositions of the invention include at least two amino acids. Suitable amino acids are selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta alanine, L-beta-homoleucine, D-beta-homoleucine, 3-aminobutanoic acid, L-2,3-diaminopropionic acid monohydrochloride, D-2, 3-diaminopropionic acid monohydrochloride, L-3-aminoisobutyric acid, D-3-aminoisobutyric acid, ethyl 3-aminobutyrate, sarcosine methyl ester hydrochloride and nipecotic acid, alkyl esters, pharmaceutically acceptable salts, and mixtures thereof. In certain embodiments, the at least two amino acids are selected from the group consisting of glycine, D-isoleucine, L-tyrosine, beta alanine, D-valine, L-isoleucine, L-valine, L-aspartic acid, D-alanine methyl ester, L-leucine, L-alanine, L-glutamine, L-lysine, L-histidine, D-alanine, L-glutamic acid, L-serine, L-proline, and mixtures thereof. In certain embodiments, the at least two amino acids are selected from the group consisting of glycine, L-alanine, L-proline, and mixtures thereof. As described below, in certain embodiments, the composition includes at least three amino acids. In one embodiment, the composition includes glycine, L-alanine, and L-proline. The compositions of the invention include from about 0.1 to about 500 mM of each amino acid.

Eosinophil peroxidase utilizes a halide as a substrate to affect its microbiocidal activity. When the site of administration of the composition of the invention does not have halide substrate sufficient to achieve the desired rate of activity, the composition further includes a halide such as chloride, bromide, and mixtures thereof.

In a preferred embodiment, the composition of the invention includes an eosinophil peroxidase, a peroxide-producing oxidase, and at least two amino acids that in combination with the eosinophil peroxidase and the oxidase enhance the composition's microbiocidal activity. As noted above, representative peroxide-producing oxidases include glucose oxidase, representative amino acids include glycine, L-alanine, L-proline, and mixtures thereof, and the composition may further include halide selected from chloride, bromide, and mixtures thereof.

The inventors have surprising found that the composition of the invention can advantageously include a relatively low concentration of eosinophil peroxidase to achieve significant killing and/or microorganism growth inhibition. Relatively low concentrations of eosinophil peroxidase increase its selectivity and limit its toxicity. The compositions of the invention can include from about 0.1 to about 100 µg/mL of eosinophil peroxidase. The compositions of the invention can also include higher concentrations of eosinophil peroxidase. In certain embodiments, the compositions include about 0.1 to about 500 µg/mL eosinophil peroxidase. In other embodiments, the compositions include about 0.1 to about 1,000 µg/mL eosinophil peroxidase. In further embodiments, the compositions include about 10 to about 10,000 µg/mL eosinophil peroxidase. In other embodiments, the composition can include from about 100 to about 50,000 µg/mL, and in certain embodiments, up to about 100,000 µg/mL eosinophil peroxidase. The microbiocidal effectiveness of representative compositions of the invention is described in Examples 2-4.

In other aspects of the invention, methods for using the eosinophil peroxidase compositions of the invention are provided.

In one embodiment, the invention provides a method for killing or inhibiting the growth of a susceptible microorganism. In the method, the microorganism is contacted with an effective amount of a composition of the invention.

In another embodiment, the invention provides a method for treating an infection in a human or animal subject. In the method, an effective amount of a composition of the invention is administering to the site of infection.

In a further embodiment, the invention provides a method of treating or preventing infection of a surgical site in a human or animal subject. In the method, an effective amount of a composition of the invention is administering to the surgical site. The nature of the surgical site is not limiting. The composition of the invention exhibits advantageous microbiocidal activity for all surgical sites. Representative surgical sites include cancer surgical sites. Cancer surgical sites include any site in which a cancerous tumor has been removed. In one embodiment, the cancer surgical site is a colorectal cancer surgical site. In another embodiment, the cancer surgical site is a brain cancer surgical site. For certain surgical sites, such as brain cancer surgical sites, the composition can be administered post-incision and pre-closure. Other suitable surgical sites that may be advantageously treated with a composition of the invention include laparoscopic surgical sites.

The compositions and methods of the invention are effective for treating polymicrobial as well as multidrug resistant infections.

In the practice of the invention, for the eosinophil peroxidase compositions that include a peroxide-producing oxidase (e.g., glucose oxidase), the eosinophil peroxidase composition is preferably administered to the site to be treated separately from the administration of the composition that includes the substrate for the oxidase (e.g., glucose). The sequence of administration is not critical; the eosinophil peroxidase composition can be administered before or after administration of the substrate composition. Thus, in a further aspect, the invention provides a binary combination that includes a first composition comprising an eosinophil peroxidase composition of the invention in an aqueous medium and a second composition comprising a substrate for the peroxide-producing oxidase in an aqueous medium.

As noted above, in certain embodiments, the invention provides an oxidative enzyme composition (e.g., EPO/GO system) that is effective as an in vivo antiseptic agent suitable for topical treatment of susceptible infections in a human or non-human mammalian subject at sites permitting direct contact of the composition with the microbial infection (e.g., surgical sites).

The composition of the invention is effective to inhibit microorganisms in situ (e.g., wound and surgical sites) that can be hostile environments for the oxidative enzyme system.

In the course of their research, the inventors sought to provide a microbiocidal system that would be robust and effective in the harshest environments (i.e., in situ wound and surgical sites). In solving the problem, the inventors surprisingly discovered that the inclusion of the specified amino acid combinations in the enzyme composition enhanced the system's microbiocidal effectiveness.

The in situ environment is a harsh environment due to the presence of serum and endogenous serum proteins. These serum proteins include enzymes that are part of the body's natural defense to damaging oxidative enzymes. In certain embodiments, the composition of the invention includes oxidative enzymes: eosinophil peroxidase and peroxide-producing oxidase. Serum proteins are active against the composition's oxidative enzymes and inhibit their activity.

As described herein, in addition to the oxidative enzyme system (e.g., EPO/GO), the composition of the claimed invention includes at least two additional amino acids selected from among the specified amino acids. The amino acids of the composition function to protect the enzyme system. The amino acid components function in a sacrificial manner and provide a temporary protective effect in situ that affords the enzyme system with a temporal window of operation. Once the amino acids of the composition are consumed by the in situ environment, the effectiveness of the oxidative enzyme system decreases. Without being bound to theory, it is believed that the amino acids of the composition protect the peroxide-producing oxidase (e.g., glucose oxidase).

The effectiveness of the composition in inhibiting microorganisms in situ is due in significant part to the protection that the specified amino acid combinations provide the composition's enzyme system.

In contrast to the amino acids useful in the composition, uses, and methods of the invention, the amino acids of the compositions described in the art (e.g., U.S. Pat. Nos. 5,389,369 and 5,888,505) do not function to protect the composition's enzyme system. Rather, the amino acids in the prior art compositions are effective to enhance microbicidal activity by targeting the microorganisms to be killed. U.S. Pat. No. 5,389,369 describes the metabolism and life cycle of yeast and sporular microorganisms. The amino acid in the system described enters the metabolic pathway for the microorganism. Fungal and bacterial spores detect the presence of certain amino acids as a signaling inducing germination thereby rendering the spores susceptible to haloperoxidase biocidal action. The prior art fails to teach or suggest the use of an amino acid to protect an eosinophil peroxidase enzyme system from the harsh in situ environment.

The in vitro activity of a representative eosinophil peroxidase formulation of the invention (C-101) against clinical isolates of target pathogens was compared to a similarly constituted myeloperoxidase formulation (E-101) as described in Example 3. Based on $MIC_{90}$ (minimum inhibitory concentration) and distribution data, the in vitro activities of E-101 and C-101 were highly comparable for all organisms studied (see Tables 1 and 2). The high level of comparability between both formulations was also reflected by scatterplot analysis whereby the MICs for E-101 and C-101 were analyzed head-to-head for each strain. With exception of nine isolates, the E-101 and C-101 MICs were the same against every strain tested. The breakout of strains for which MIC differences were encountered were as follows: (a) seven strains had C-101 MICs that were one doubling dilution lower than the E-101 MICs, these strains were comprised of one strain each of S. aureus, E. faecalis, E. coli, and four strains of P. aeruginosa; and (b) two strains (both K. pneumoniae) had E-101 MICs that were one doubling dilution lower than the C-101 MICs. The results are set forth below in Tables 1, 2a, and 2b.

The time kill of a representative eosinophil peroxidase solution of the invention (C-101) against select gram-positive and gram-negative ATCC organisms was compared to a similarly constituted myeloperoxidase formulation (E-101) as described in Example 4.

The summary data used to produce the time kill curves for each organism tested against C-101 and E-101 are provided in Tables 3 and 4, respectively.

For S. aureus ATCC 29213 the time kill kinetics for C-101 and E-101 were similar. Bactericidal activity (defined as a >3 $log_{10}$ decrease in CFU's/ml compared to the starting inoculum) was achieved within four hours regardless of the concentrations of C-101 or E-101 tested.

For E. faecalis ATCC 29212 C-101 and E-101 bactericidal activity within four hours was achieved only at concentrations of 16, 64, and 256 µg/ml. Cidality was not achieved at 24 hours for either formulation at concentrations of 0.06 and 0.25 µg/ml, respectively (Tables 3 and 4). Cidality was achieved at 24 hours at concentrations of 1 and 4 µg/ml for both formulations.

For E. coli ATCC 29212 bactericidal activity was achieved by each formulation at every concentration tested except 0.06 µg/ml. At this lowest concentration neither formulation achieved cidality even after 24 hours (Tables 3 and 4).

For P. aeruginosa ATCC 27853 both C-101 and E-101 were bactericidal by four hours at every concentration tested.

As illustrated by the time kill kinetic study, the inventors surprisingly discovered that C-101 was vastly more effective that the corresponding myeloperoxidase composition E-101 with regard to killing S. aureus and E. coli as demonstrated by comparing the kill kinetics at the 64 µg/mL eosinophil peroxidase concentration. Referring to Tables 3 and 4, while C-101 effectively killed S. aureus and E. coli by the 0.03 hour time point (see Table 3), E-101 achieved the same level of kill only after 4 hours (see Table 4).

Representative embodiments of the compositions and methods of the invention are further discussed below.

In one particularly preferred embodiment, the compositions and methods of the invention are used as antiseptic agents exhibiting enhanced eosinophil peroxidase antimicrobial activity against a broad range of pathogenic microorganisms including bacteria and fungi. In one aspect, the compositions and methods of the invention are highly suitable for the topical treatment of susceptible infections in a human or non-human mammalian subject at sites permitting direct contact of the compositions of the invention with the microbial infection, such as, for example, infections of the skin, eyes, ears, mouth, nasal and sinus passages, traumatic injury sites, surgical sites and the like. For use in contact with host tissue, the antiseptic systems are based on the use of dioxygenating eosinophil peroxidase which exhibits selective affinity for pathogenic microorganisms. As such, high potency microbiocidal action can be directed to the target microorganisms without associated host tissue destruction or disruption of normal flora; i.e., the antiseptic action is selective and confined to the target microorganism.

Thus, in one embodiment, the invention provides compositions for inhibiting the growth of susceptible microorganisms comprising eosinophil peroxidase and at least two amino acids that work alone or in combination, in the presence of peroxide and chloride or bromide, to enhance the microbiocidal activity of the eosinophil peroxidase. The compositions may additionally comprise hydrogen peroxide or a source of hydrogen peroxide, and chloride or bromide, when not otherwise available in sufficient amounts at the site of use of the compositions. In a related embodiment, the invention provides methods of treating a human or animal subject in need of such treatment comprising administering to a site of infection in the subject a composition comprising eosinophil peroxidase and at least two amino acids that work alone or in combination to enhance the microbiocidal activity of the eosinophil peroxidase. Again, the composition may additionally comprise hydrogen peroxide or a source of hydrogen peroxide, and chloride or bromide, to supplement naturally occurring amounts at the infection site.

In other embodiments, the invention provides compositions and methods for inhibiting the growth of susceptible microorganisms in vitro, particularly in applications where biomedical devices, such as bandages, surgical instruments, suturing devices, catheters, dental appliances, contact lenses and the like, require disinfection or sterilization and where the device is to be subsequently contacted with host tissue. Thus, high potency eosinophil peroxidase formulations of the invention can serve as in vitro disinfecting or sterilizing preparations. By limiting the time period of hydrogen peroxide availability, eosinophil peroxidase-enhanced formulations can be made sufficiently potent to insure disinfection and even sterilization of a material or device before contact with host tissue. Any potential toxicity to normal flora and host tissue associated with the use of these high potency formulations ceases when peroxide is depleted, and as such, the formulation-treated material or device can be brought in contact with host tissue without additional washing or detoxification.

Thus, in one embodiment, the invention provides methods for killing or inhibiting growth of susceptible microorganisms in vitro comprising contacting the microorganisms, in the presence of hydrogen peroxide and chloride or bromide, with a composition comprising eosinophil peroxidase and at least two amino acids that work alone or in combination to enhance the microbiocidal activity of the eosinophil peroxidase.

Representative compositions of the invention comprise (1) eosinophil peroxidase (EPO), (2) at least two activity enhancing amino acids, and optionally (3) hydrogen peroxide ($H_2O_2$) or a source of $H_2O_2$, and (4) chloride or bromide.

Eosinophil peroxidase useful in the present invention is a halide:hydrogen peroxide oxidoreductase for which halide (i.e., chloride, bromide, or iodide) or pseudo-halide (e.g., thiocyanate), is the electron donor or reductant and peroxide is the electron receiver or oxidant. The enzymatic activity of a eosinophil peroxidase solution can be determined by reaction with guaiacol in the presence of hydrogen peroxide in sodium phosphate buffer. The reaction generates a product with strong absorbance at 470 nm. The activity is determined from the kinetics of the increase in absorbance compared to a reference standard. Eosinophil peroxidase (EPO) activity is commonly expressed in guaiacol units/mL (GU/mL), and is also expressed as micrograms of EPO per milliliter (μg/mL). The conversion of μg to GU of EPO is based on 0.375 GU per μg of EPO. The specific activity is calculated from its activity and the total protein concentration and expressed in GU/mg protein. Useful amounts of eosinophil peroxidase employed in the compositions of the invention will vary widely depending on conditions under which the compositions are employed, the environment of use and the desired result. For most purposes, the compositions of the invention will generally comprise at least about 0.05 μg/ml (0.055 GU/ml) of eosinophil peroxidase. In some embodiments, the compositions of the invention will comprise from about 1 to about 50,000 μg/ml of eosinophil peroxidase (i.e., from about 1.1 to about 55,000 GU/ml), more preferably from about 5 to about 10,000 μg/ml of eosinophil peroxidase (i.e., from about 5.5 to about 11,000 GU/ml), and even more preferably from about 10 to about 5,000 μg/ml of eosinophil peroxidase (i.e., from about 11 to about 5,500 GU/ml).

Inclusion of at least two activity enhancing amino acids, as described in detail herein, greatly increases the microbiocidal capacity of the oxidase-eosinophil peroxidase system against susceptible microorganisms. Amino acids useful in the practice of the invention are those amino acids that, when used alone or in combination and in the presence of peroxide and chloride or bromide, enhance the antimicrobial activity of the eosinophil peroxidase antimicrobial system against susceptible microorganisms. At least two amino acids are used at concentrations that do not produce adverse effects on the eosinophil peroxidase activity of the system or undesirable effects in the environment of use of the compositions and methods.

In some embodiments, the compositions of the invention comprise at least two amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, and ethyl 3-aminobutyrate, as well as the alkyl esters thereof, such as, for example, L-alanine methyl ester, D-alanine methyl ester, L-lysine methyl ester dihydrochloride, glycine methyl ester hydrochloride, L-proline methyl ester hydrochloride, L-valine ethyl ester hydrochloride and ethyl 2-aminopropanoate, and N-substituted amino acids, such as sarcosine methyl ester hydrochloride and nipecotic acid.

In other embodiments, the compositions of the invention comprise at least two amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, as well as alkyl esters thereof.

In some embodiments, the compositions of the invention comprise eosinophil peroxidase and at least three amino acids that work alone or in combination to enhance eosinophil peroxidase microbiocidal activity. Accordingly, in some embodiments, the compositions of the invention comprise at least three amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, D-valine, beta amino acids, such as beta alanine, L-beta-homoleucine, D-beta-homoleucine, 3-aminobutanoic acid, L-2,3-diaminopropionic acid monohydrochloride, D-2,3-diaminopropionic acid monohydrochloride, L-3-aminoisobutyric acid, D-3-aminoisobutyric acid, and ethyl 3-aminobutyrate, as well as esters thereof, such as, for example, L-alanine methyl ester, D-alanine methyl ester, L-lysine methyl ester dihydrochloride, glycine methyl ester hydrochloride, L-proline methyl ester hydrochloride, L-valine ethyl ester hydrochloride and ethyl 2-aminopropanoate, and N-substituted amino acids, such as sarcosine methyl ester hydrochloride and nipecotic acid.

In still other embodiments, the compositions of the invention comprise at least three amino acids selected from the group consisting of glycine, L-alanine, D-alanine, L-alanine anhydride, L-glutamine, L-glutamic acid, glycine anhydride, hippuric acid, L-histidine, L-leucine, D-leucine, L-isoleucine, D-isoleucine, L-lysine, L-ornithine, D-phenylalanine, L-phenylalanine, L-proline, L-hydroxyproline, L-serine, taurine, L-threonine, D-threonine, L-tyrosine, L-valine, and D-valine, as well as esters thereof. In one presently preferred representative example of this aspect of the invention, the compositions of the invention comprise eosinophil peroxidase and the amino acids glycine, L-alanine and L-proline, in amounts effective to enhance the antimicrobial activity of eosinophil peroxidase.

Useful amounts of the amino acids employed in the compositions of the invention will vary depending on amount of eosinophil peroxidase in the compositions and conditions present in the environment of use. For most purposes, the compositions of the invention will generally comprise from about 0.01 to about 500 mM, more preferably from about 0.1 to about 100 mM, and even more preferably from about 0.3 to about 50 mM of each of the amino acids of the invention.

Because the antiseptic activity of the eosinophil peroxidase compositions of the invention involves the reaction of peroxide and chloride or bromide to form hypohalite (hypohalide), and the reaction of peroxide and hypohalite (hypohalide) to form singlet molecular oxygen, the activity of the compositions of the invention is dependent upon the presence, at the site of antimicrobial activity, of a suitable peroxide and halide. In some situations, peroxide (e.g., hydrogen peroxide) may be present at the site activity due, for example, to the activity of naturally occurring flora, and sufficient amounts of chloride may be present in the physiological milieu to act as a cofactor in the conversion reaction. In these situations, no additional peroxide or halide need be administered or included in the compositions of the invention. In other situations, it may be necessary or desirable to additionally provide hydrogen peroxide and/or halide at the site of microbial treatment. Accordingly, the compositions of the invention may additionally comprise, if desired, a peroxide or agent capable of producing peroxide in vivo or in vitro and chloride or bromide.

Peroxides useful in the compositions and methods of the invention include hydrogen peroxide, alkyl hydroperoxides of the formula:

wherein R is hydrogen or a short chain alkyl group having from 1 to 3 carbon atoms, and inorganic peroxides, such as boroperoxide or ureaperoxide. The oxidant activity of the organic peroxides generally decreases with increasing R chain length, as follows:

The presently preferred peroxide for use in the compositions of the invention is hydrogen peroxide. Hydrogen peroxide may also be made available at the site of the antimicrobial activity by including in the composition an agent capable of producing hydrogen peroxide in vivo or in vitro. Particularly useful agents for this purpose include, for example, oxidases, such as glucose oxidase, cholesterol oxidase, and galactose oxidase.

When hydrogen peroxide is directly included in compositions of the invention for in vivo applications, the amounts employed are preferably designed to provide maximum disinfecting activity. Damage to host cells and tissue and to normal flora is avoided by avoiding direct contact during the period of high $H_2O_2$ exposure. Accordingly, the compositions of the invention may comprise from about 1 nmol to about 10 μmol of hydrogen peroxide per ml of composition, more preferably from about 5 nmol to about 5 μmol of hydrogen peroxide per ml of composition, and most preferably from about 10 nmol to about 1 mmol of hydrogen peroxide per ml of composition. Agents capable of producing hydrogen peroxide in vivo, e.g., peroxide producing oxidases, are particularly useful for dynamic control of the amounts of hydrogen peroxide present at the site of antimicrobial activity. Such agents maximize antimicrobial activity of the composition by providing and maintaining a steady, low level concentration of $H_2O_2$. Accordingly, the amount of such agents to be employed will be highly dependent on the nature of the agent and the effect desired, but will preferably be capable of producing a steady state level of from about 1 pmol to about 1 μmol of hydrogen peroxide per ml of liquid per minute, depending on the type and concentration of halide available at the site of antimicrobial activity. When the formulation is to be used as a disinfectant-sterilizing solution, the oxidase and its substrate can be adjusted to provide relatively high steady-state concentrations of $H_2O_2$ lasting for the required sterilization period. The disinfection-sterilizing action is terminated with exhaustion of the oxidase substrate or relative to the rate of oxidase degradation. As a representative example, when the oxidase is glucose oxidase and its substrate is glucose, the compositions of the invention may comprise from about 0.05 to about 3,000 U/ml, more preferably from about 0.1 to about 1,000 U/ml, and even more preferably from about 1 to about 500 U/ml of glucose oxidase, and from about 0.1 to about 1,000 mM, more preferably from about 0.5 to about 800 mM, and even more preferably from about 1 to about 500 mM glucose.

When bromide or chloride are included in the compositions of the invention, the use, selection and amount of bromide or chloride employed in a particular application will depend upon various factors, such as the desired therapeutic effect, the availability of peroxide and other factors. Because chloride is present in most physiological media at levels sufficient to be non-limiting as the halide cofactor, an external source of chloride is generally not required. When an external source of chloride is desired, the amount of chloride employed will preferably fall in the range of about 10 µmol chloride to about 150 µmol chloride per ml of solution to approximate physiological conditions. When included, the compositions of the invention may comprise from about 1 nmol bromide to about 20 µmol bromide per ml of liquid composition, more preferably from about 10 nmol bromide to about 10 µmol bromide per ml of liquid composition, and most preferably from about 100 nmol bromide to about 1 µmol bromide per ml of liquid composition.

The ratio of halide to peroxide is an important consideration in formulating an effective microbiocidal environment. Accordingly, in addition to ensuring effective levels of halide and peroxide at the situs of microbial attack, as described above, it is preferable to practice the methods of the invention at halide:peroxide ratios that provide optimal microbiocidal activity. For example, when the halide is $Cl^-$ (chloride), the ratio of $Cl^-$ to peroxide is preferably maintained in the range of about 1 to about 40,000 in the environment of microbiocidal activity, more preferably from about 50 to about 40,000 and most preferably from about 200 to about 40,000. When the halide is $Br^-$ (bromide), the ratio of $Br^-$ to peroxide is preferably maintained in the range of about 0.1 to about 4,000 in the environment of microbiocidal activity, more preferably from about 0.5 to about 2,000 and most preferably from about 1 to about 1,000.

Representative formulations of the invention were evaluated as described in Example 1. The formulations were evaluated for pH, bromide concentration, hydrogen peroxide concentration, and glucose oxidase concentration in an in vitro eosinophil peroxidase assay adapted from U.S. Pat. No. 7,108,997 B2. The results of the evaluations are illustrated in FIGS. 1-4.

As noted above, the formulations of the invention can be prepared by combining an enzyme formulation and a substrate formulation.

A representative enzyme formulation is a solution of eosinophil peroxidase (p-EPO, 2.5 mg/mL), glucose oxidase (0.5 mg/mL), L-alanine (20 mM), L-proline (20 mM), and glycine (20 mM) in sodium phosphate (20 mM, pH 6.5), sodium chloride (150 mM), potassium bromide (2 mM), and TWEEN 80 (0.1%, v/v).

A representative substrate formulation is a solution of glucose (100 mM) in sodium phosphate (20 mM, pH 6.5), sodium chloride (150 mM), potassium bromide (2 mM), and TWEEN 80 (0.02%, v/v).

As an illustrative example, a composition suitable for use as an antimicrobial (or anti-infective) solution may comprise from about 1 to 50,000 µg/ml (i.e., from about 1.1 to about 55,000 GU/ml) of eosinophil peroxidase, from 0.1 to 500 µmol/mL (i.e., from 0.1 to 500 mM) of glycine, from 0.1 to 500 µmol/mL (i.e., from 0.1 to 500 mM) of L-proline, from 0 to 100 mmol/mL (i.e., from 0 to 100 mM) of L-alanine, from 0.01 to 500 units of glucose oxidase, and from 50 to 500 mEq/L of bromide. The above composition is combined with from 1 to 500 mmol/mL (i.e., from 1 to 500 mM) of glucose or dextrose and used as a liquid disinfectant or sterilizing solution. The combination can occur by first applying the EPO composition to the site of infection followed by applying glucose or dextrose composition, or vice versa.

The compositions and methods of the invention can be used to inhibit the growth of a broad spectrum of pathological microorganisms, preferably with a minimum of damage to normal flora. As demonstrated in the examples, compositions of the invention are highly efficient in the inhibition of both Gram-positive and Gram-negative organisms, as, for example, *Enterococcus faecalis*, *Enterococcus faecium*, *Staphylococcus aureus*, *Staphylococcus epidermidis*, *Streptococcus agalactiae*, *Streptococcus* Group C, *Streptococcus* Group F, *Streptococcus* Group G, *Streptococcus pyogenes*, *Citrobacter freundii*, *Enterobacter cloacae*, *Escherichia coli*, *Klebsiella pneumoniae*, *Proteus mirabilis*, *Acintobacter* spp., *Pseudomonas aeruginosa*, *Aeromonas hydrophilia*, and *Pasteurella multocida*. In addition, the compositions of the invention are useful in the inhibition of spore forming microorganisms such as, for example, bacteria such as *Bacillus* sps. and *Clostridium* sps., and fungi such as *Aspergillis* sps., *Fusarium* sps., and *Trichophyton* sps. Due to their wide spectrum of activity, in some embodiments the compositions of the invention may be advantageously used in the treatment, of polymicrobial infections. Polymicrobial diseases involve multiple infectious agents and are referred to as complex, complicated, mixed, dual, secondary, synergistic, concurrent, polymicrobial, or coinfections. Polymicrobial diseases include, for example, infections associated with abscesses, AIDS-related opportunistic infections, conjunctivitis, gastroenteritis, hepatitis, multiple sclerosis, otitis media, periodontal diseases, respiratory diseases, and genital infections. In addition, since the compositions of the invention operate by an entire different mechanism of action than those involved in conventional antibiotic therapy, in some embodiments the compositions of the invention are also highly useful in the treatment of infections caused, at least in part, by multidrug resistant pathogens, such as MRSA (methicillin-resistant *Staphylococcus aureus*), VRSA (Vancomycin-resistant *S. aureus*), VRE (Vancomycin-Resistant *Enterococcus*), Penicillin-Resistant *Enterococcus*, PRSP (Penicillin-resistant *Streptococcus pneumoniae*), isoniazid/rifampin-resistant *Mycobacterium tuberculosis* and other antibiotic-resistant strains of *E. coli*, *Salmonella*, *Campylobacter*, and Streptococci. Such bacteria are herein referred to as "antibiotic-resistant" or "drug-resistant" or "multidrug-resistant", or by other similar terms that are well understood in the art.

As used herein, the term "normal flora" means bacteria, which normally reside in or on body surfaces of a healthy host at symbiotic levels. Normal flora include, for example, the lactic acid family of bacteria in the mouth, intestine, or vagina of human subjects, e.g., *Streptococcus* (viridans) in the mouth, and *Lactobacillus* sp. (e.g., Tissier's *bacillus* and Doderlein's *bacillus*) in the intestines of breast-fed infants, external genitalia, anterior urethra and vagina. Microorganisms which constitute normal flora of a host are well known (e.g., see *Principles and Practice of Infectious Diseases*, supra, New York, pp. 34-36 and 161). It has been found that the eosinophil peroxidase of the invention selectively bind to many pathogenic bacteria and fungi in preference over normal flora. In in vivo applications, the host is preferably treated with an amount of eosinophil peroxidase which is ineffective to eliminate normal flora from the host. In in vitro applications for disinfection-sterilization, sufficiently high concentrations of eosinophil peroxidase can be employed to ensure complete killing of all vegetative and yeast forms. Under such conditions, damage to host tissue and normal flora is avoided by consumption of $H_2O_2$ or the $H_2O_2$-generating system prior to contact with the host tissue.

The bioactivity of representative eosinophil peroxidase (EPO) formulations is described in Example 2 and illustrated in FIGS. 5-10.

The assay described in Example 2 clearly demonstrates that added bromide was not critical when the pH was 5.5. It is important to note that standard assay conditions used phosphate buffered saline, the NaCl concentration of which was 150 mM. Many report the utilization of chloride by EPO at low pH. But no steps were taken to ensure that bromide ions were not present in buffer or microbes. Note that at pH ≥6.5 no kill was observed in the absence of added bromide.

These studies demonstrated that the two enzymes, p-EPO and GO, can control growth in complex media (TSB) at neutral pH (pH 7.4). Glucose concentration in TSB is about 30 mM (physiologic glucose is about 5 mM). First study used low (0.1 mM) bromide, then again at higher (1.0 mM) bromide. At higher bromide concentration, p-EPO/GO (≥0.2 µg/mL) completely blocked $S.$ $aureus$ growth. These demonstrate the requirement of higher bromide at neutral pH.

The compositions of the invention generally comprise amounts of eosinophil peroxidase and at least two amino acids which are effective, in the presence of a peroxide and a halide to kill or inhibit the growth of susceptible microorganisms. The compositions may additionally comprise a pharmaceutically acceptable carrier. In some embodiments, the compositions may be conveniently provided in a liquid carrier. Any liquid carrier may be generally used for this purpose, provided that the carrier does not significantly interfere with the selective binding capabilities of the eosinophil peroxidase or with enzyme activity. Alternatively, the compositions may be provided in solid form with activation on solubilization in liquid.

As set forth above, the compositions of the invention may additionally comprise peroxide or an agent capable of producing peroxide, such as an oxidase, as described in detail above. The oxidase-eosinophil peroxidase system lends itself to construction as a binary formulation in which the composition active agents are formulated in two separate parts for consolidation at the time of use. For example, one part of the binary formulation may comprise a solution containing the oxidase, the eosinophil peroxidase and at least two activity-enhancing amino acids, e.g., glycine, L-alanine and L-proline. In one embodiment, the first part of the binary formulation comprises an eosinophil peroxidase, a peroxide-producing oxidase, and amino acids glycine, L-alanine, and L-proline. The second part of the binary may comprise a substrate for the oxidase, e.g., glucose or dextrose in the case of glucose oxidase or molecular oxygen, $O_2$. In some embodiments, the first part of the binary formulation, the second part of the binary formulation, or both the first part and the second part further comprise a halide. In some embodiments, the halide is bromide, chloride, or mixtures thereof. The substrate may be provided, for example, in the form of a solid wafer. For sterilization of an article, e.g., a surgical instrument or a contact lens, the substrate wafer may be placed in a sterilization chamber along with the item to be sterilized. The eosinophil peroxidase, activity enhancing amino acids and oxidase is added to initiate sterilization. In some embodiments, the eosinophil peroxidase composition may additionally comprise alcohol in order to facilitate oxidase substrate solubilization and utilization by the oxidase. This system will produce sustained microbiocidal action as long as sufficient substrate is present to drive the reaction.

The compositions of the invention may be administered alone or in combination with one or more other therapeutic agents. Representative additional therapeutic agents that may be used in combination with the compositions of the invention include, for example, antibiotic or antiseptic agents such as anti-bacterial agents, anti-fungicides, anti-viral agents and/or anti-parasitic agents. In some embodiments, the additional therapeutic agents may be one or more penicillins, cephalosporins, carbacephems, cephamycins, carbapenems, monobactams, aminoglycosides, glycopeptides, quinolones, tetracyclines, macrolides, and/or fluoroquinolones. In some embodiments, the additional therapeutic agents may be iodine, silver, copper, chlorhexidine, polyhexanide, biguanides, chitosan and/or acetic acid. The one or more additional therapeutic agents of the invention may be incorporated as part of the same composition or may be administered separately.

For in vivo applications, the antiseptic compositions can be administered in any effective pharmaceutically acceptable form to warm blooded animals, including human and animal subjects, e.g., in topical, lavage, oral, vaginal or suppository dosage forms, as a topical, buccal, nasal spray, aerosol for inhalation or in any other manner effective to deliver active eosinophil peroxidase to a site of microorganism infection. The route of administration will preferably be designed to obtain direct contact of the antiseptic compositions with the infecting microorganisms. In one aspect of the invention, the compositions of the invention are delivered or administered topically to areas of a human or animal subject that are susceptible to infection, such as, for example, to the gums, eyes, ears, skin, wounds, vaginal areas, groin areas, bed sores, burns, areas under medical dressings, diapers or other coverings which are likely to be moist, and the like.

For topical applications, the pharmaceutically acceptable carrier may take the form of liquids, creams, foams, lotions, ointments, suspensions, suppositories or gels, and may additionally comprise aqueous or organic solvents, buffering agents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration. In addition, the compositions of the invention may be impregnated in dressings or coverings for application to a subject.

In another embodiment of the invention, the compositions of the invention may be specifically designed for in vitro applications, such as disinfecting or sterilization of medical devices, contact lenses and the like, particularly where the devices or lenses are intended to be used in contact with a patient or wearer. For applications of this type, the compositions may be conveniently provided in the form of a liquid, cream, foam, lotion or gel, and may be provided with emulsifiers, surfactants, buffering agents, wetting agents, preservatives, and other components commonly found in compositions of this type. Compositions of the invention may be impregnated into absorptive materials, such as sutures, bandages, and gauze, or coated onto the surface of solid phase materials, such as staples, zippers and catheters to deliver the compositions to a site for the prevention of microbial infection. Other delivery systems of this type will be readily apparent to those skilled in the art.

Other components, such as an oxidase for peroxide generation, substrate for the oxidase and halide may be included, as desired, as described in detail above. In addition, the components may be formulated in a single formulation, or may be separated into binary formulations for later mixing during use, as may be desired for a particular application. For single formulations, one required system component which is available at the application site, such as halide, oxidase, prosthetic group for the oxidase, reducing substrate for the oxidase, or molecular oxygen is preferably left out of the formulation to preclude premature reaction and exhaustion of system components.

The foregoing may be better understood in connection with the following representative examples, which are presented for purposes of illustration and not by way of limitation.

EXAMPLES

Example 1

Representative Eosinophil Peroxidase Formulations

In this example, representative eosinophil peroxidase formulations are described. The formulations were evaluated for pH, bromide concentration, hydrogen peroxide concentration, and glucose oxidase concentration in an in vitro assay adapted from U.S. Pat. No. 7,108,997 B2. The eosinophil peroxidase was p-EPO (Porcine Eosinophil Peroxidase Lot R102307, Exoxemis, Inc., Omaha, Nebr.).

pH v. Bromide Concentration

As shown in FIG. 1, p-EPO catalyzes the formation of N-bromotaurine. This reaction is likely indirect, as p-EPO catalyzes hypobromous acid formation from hydrogen peroxide, which then reacts with the free amine group of taurine to form N-bromotaurine. Quantitation of N-bromotaurine is achieved by oxidation of the dye 3,3',5,5' dimethylbenzidine in the presence of potassium iodide. Evident in FIG. 1, the reaction is optimal at pH 6.5 in the presence of ≥2 mM bromide. It is important to note, however, that this may not only reflect the enzyme's rate of catalysis, but also the rate of taurine bromination. Also at pH ≤6.5, chloride ions may substitute for bromide ions during p-EPO catalysis (Biochem J. (2001) 358, 233-239). Because the reaction is buffered with Na phosphate (20 mM) containing NaCl (150 mM) and TWEEN 80 (0.02%, v/v) absorbance values may reflect the amount of N-bromotaurine and/or N-chlorotaurine.

Bromide Concentration at pH 6.5

Figure 2:
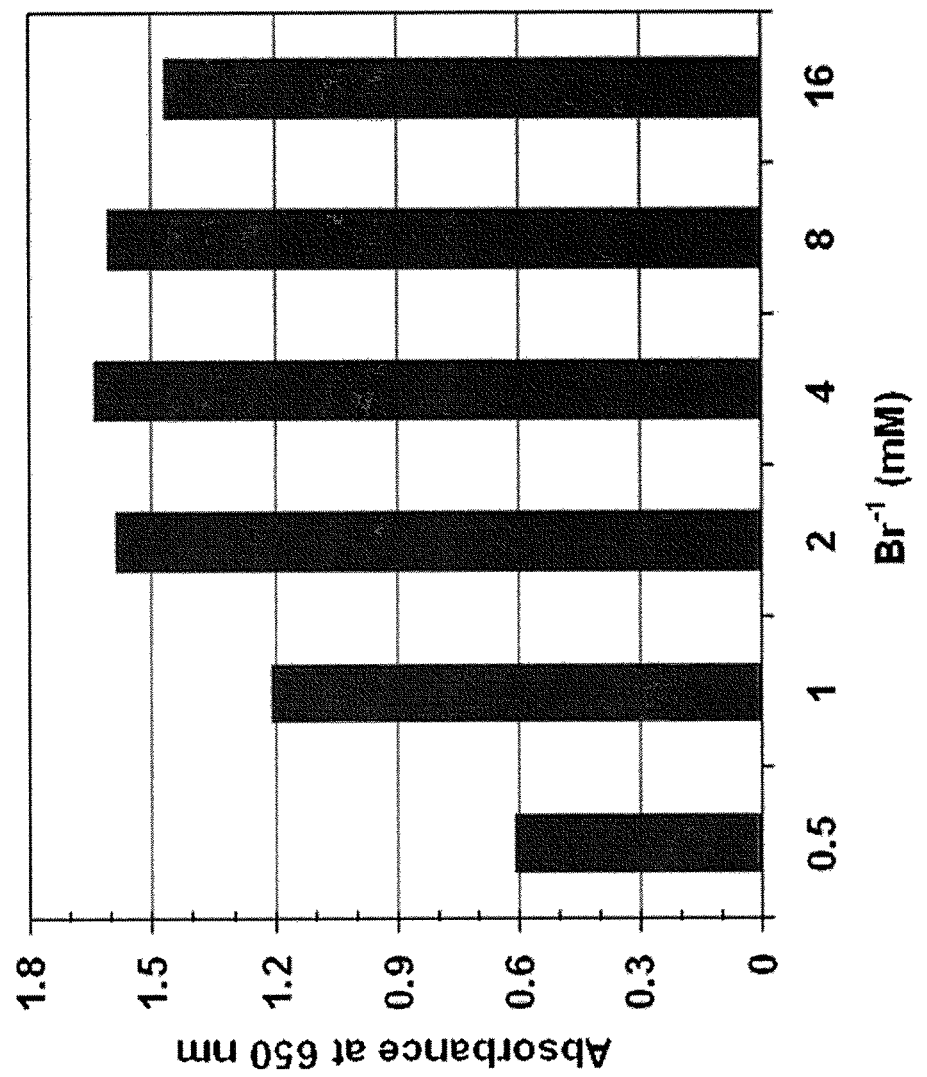
FIG. 2 is a graph comparing eosinophil peroxidase (p-EPO) activity as a function of bromide concentration (0.5, 1, 2, 4, 8, 16 mM) at pH 6.5 (p-EPO 54 ng/mL, $H_2O_2$ 0.1 mM, 10 min assay).

At pH 6.5, the rate of catalysis is supported at bromide concentrations of 2-16 mM (FIG. 2).

pH v. Hydrogen Peroxide Concentration

Figure 3:
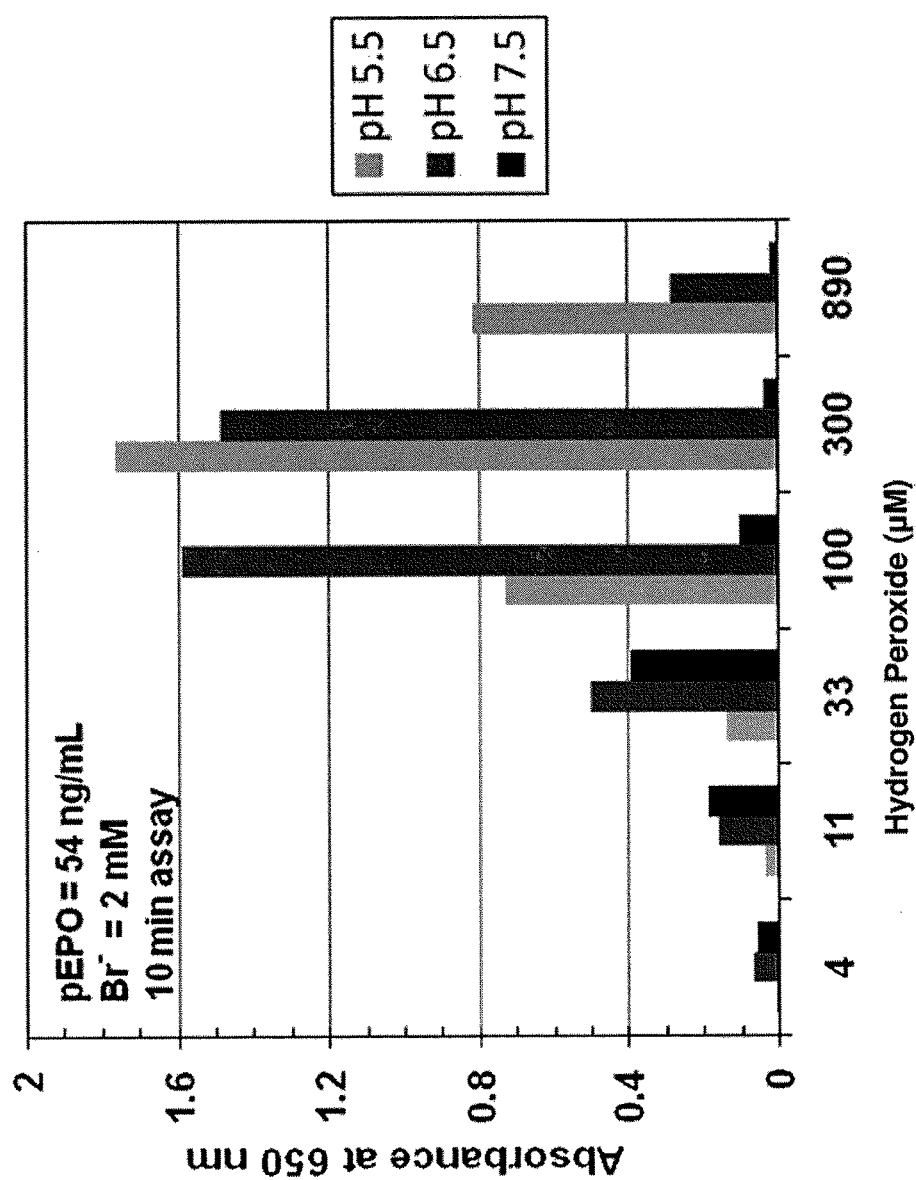
FIG. 3 is a graph comparing eosinophil peroxidase (p-EPO) activity as a function of pH (5.5, 6.5, and 7.5) and hydrogen peroxide concentration (4, 11, 33, 100, 300, 890 µM) in an in vitro assay quantitating N-bromotaurine by oxidation of 3,3',5,5'-dimethylbenzidine (absorbance at 650 nm) (p-EPO 54 ng/mL, bromide 2 mM, 10 min assay).

At pH 6.5, the rate of catalysis is highest at hydrogen peroxide concentrations of 100-300 μM; at pH 5.5, a high rate is observed at 300 μM hydrogen peroxide (FIG. 3).

Reaction Rate Using Glucose Oxidase as the Source for Hydrogen Peroxide

Figure 4:
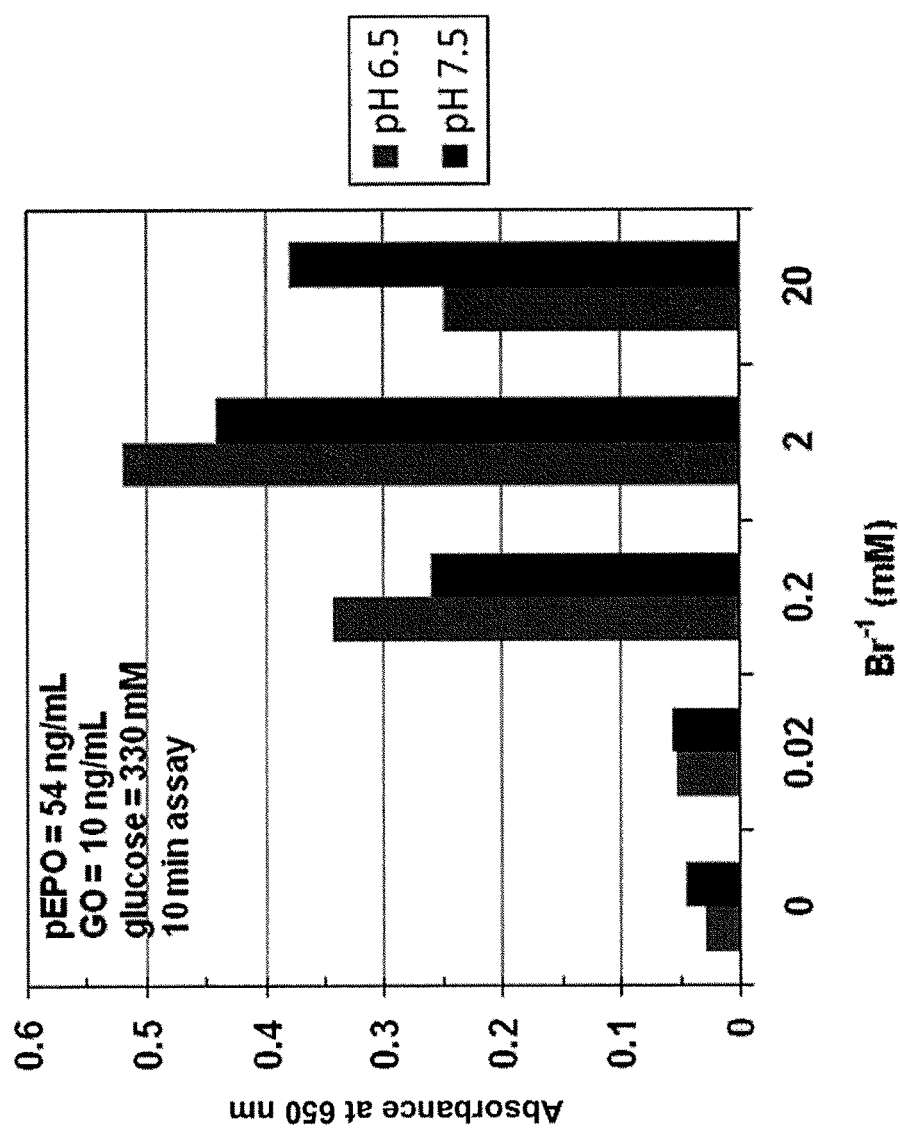
FIG. 4 is a graph comparing eosinophil peroxidase (p-EPO) activity as a function of pH (6.5 and 7.5) and bromide concentration (0, 0.02, 0.2, 2, 20 mM) in an in vitro assay quantitating N-bromotaurine by oxidation of 3,3',5,5'-dimethylbenzidine (absorbance at 650 nm) using glucose oxidase (GO) as the hydrogen peroxide source (p-EPO 54 ng/mL, GO 10 ng/mL, glucose 330 mM, 10 min assay).
Figure 5A:
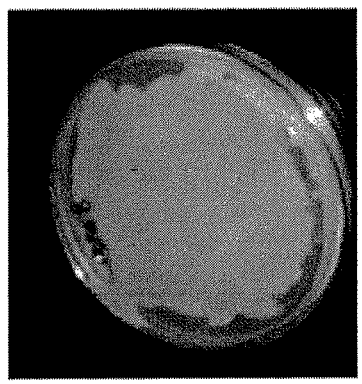
FIGS. 5A-5H are images of S. aureus cultures demonstrating eosinophil peroxidase (p-EPO) activity as a function glucose concentration (5A and 5B, no glucose; 5C and 5D, +10 mM glucose; 5E and 5F, +50 mM glucose; 5G and 5H, +200 mM glucose) An aliquot (10 µl of Enzyme Solution (0.1 mg/mL p-EPO) was added to Substrate Solution (1.0 mL+/−glucose) at room temperature; final [p-EPO] was 1 µg/mL, and final KBr was 1 mM; inoculate using S. aureus (10 µL, $10^9$ CFU/mL), final [S. aureus] was $10^7$ CFU/mL; incubate 5 min at room temperature; and plate 0.1 mL.
Figure 5B:
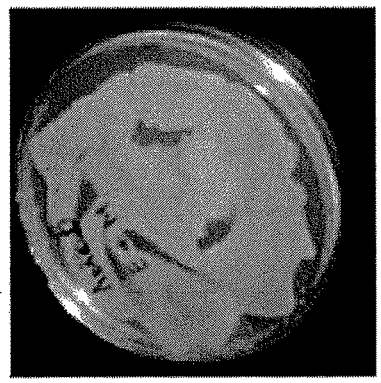
Figure 5C:
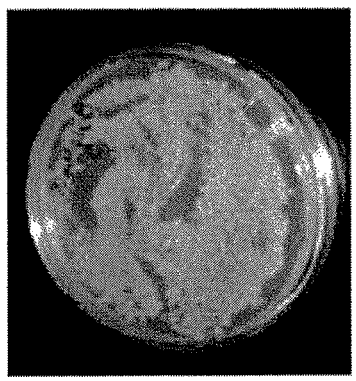
Figure 5D:
Figure 5E:
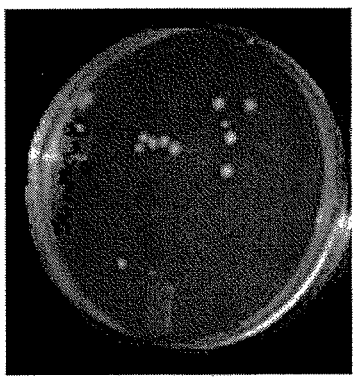
Figure 5F:
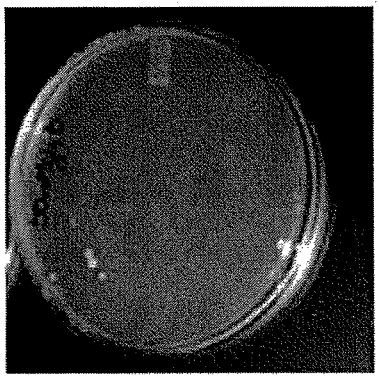
Figure 5G:
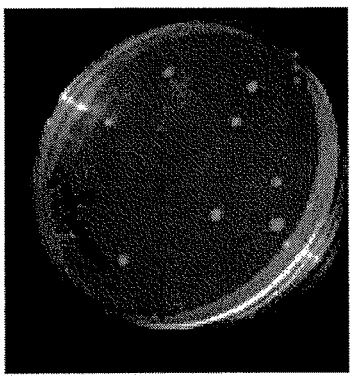
Figure 5H:
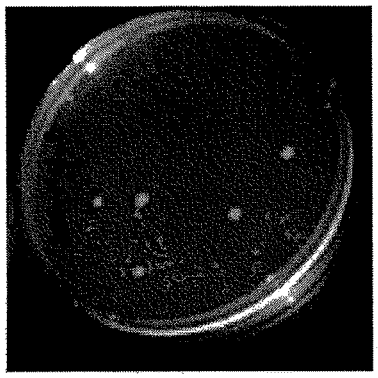

The N-bromotaurine reaction was investigated using glucose oxidase (GO) as a hydrogen peroxide source. Glucose oxidase and glucose was added to the reaction mixture in place of hydrogen peroxide. Glucose oxidase was used at a p-EPO/GO ratio of 5.4/1 (w/w), the preceding data suggested that p-EPO is most efficient when the hydrogen peroxide is 0.03-0.3 mM. As shown in FIG. 4, using these conditions the reaction was most rapid when bromide was 2 mM. The pH dependence was less apparent when GO was used in place of hydrogen peroxide, but note the lower yield (absorbance at 650 nm) when compared to reactions using hydrogen peroxide (FIG. 1).

Example 2

Bioactivity of Representative Eosinophil Peroxidase Formulations

In this example, the bioactivity of representative eosinophil peroxidase (EPO) formulations is described.

Bioactivity Vs. Glucose Concentration at pH 6.5

To explore p-EPO bioactivity, survival of *Staphylococcus aureus* in a Suspension/Neutralization Kill Assay was employed. Glucose oxidase was used as a hydrogen peroxide source and survival (5 minutes at room temperature) was measured in the presence of varying glucose concentrations (FIGS. 5A-5H). Evident is the high kill at glucose concentrations ≥50 mM (FIGS. 5E-5H).

In this example, unless stated otherwise, stock Enzyme Solution was p-EPO (2.7 mg/mL), glucose oxidase (0.5 mg/mL), L-alanine (16.8 mM), L-proline (21.6 mM), and glycine (21.6 mM) in sodium phosphate (20 mM), sodium chloride (150 mM), potassium bromide (varying concentrations), and TWEEN 80 (0.02%, v/v); Substrate Solution was glucose (varying concentrations) in sodium phosphate (20 mM), sodium chloride (150 mM), potassium bromide (varying concentrations), and TWEEN 80 (0.02% v/v); and Sample Dilution Buffer was sodium phosphate (20 mM, pH 6.5), sodium chloride (150 mM), potassium bromide (2 mM), and TWEEN 80 (0.1%, v/v).

pH v. Bromide Concentration

Figure 6:
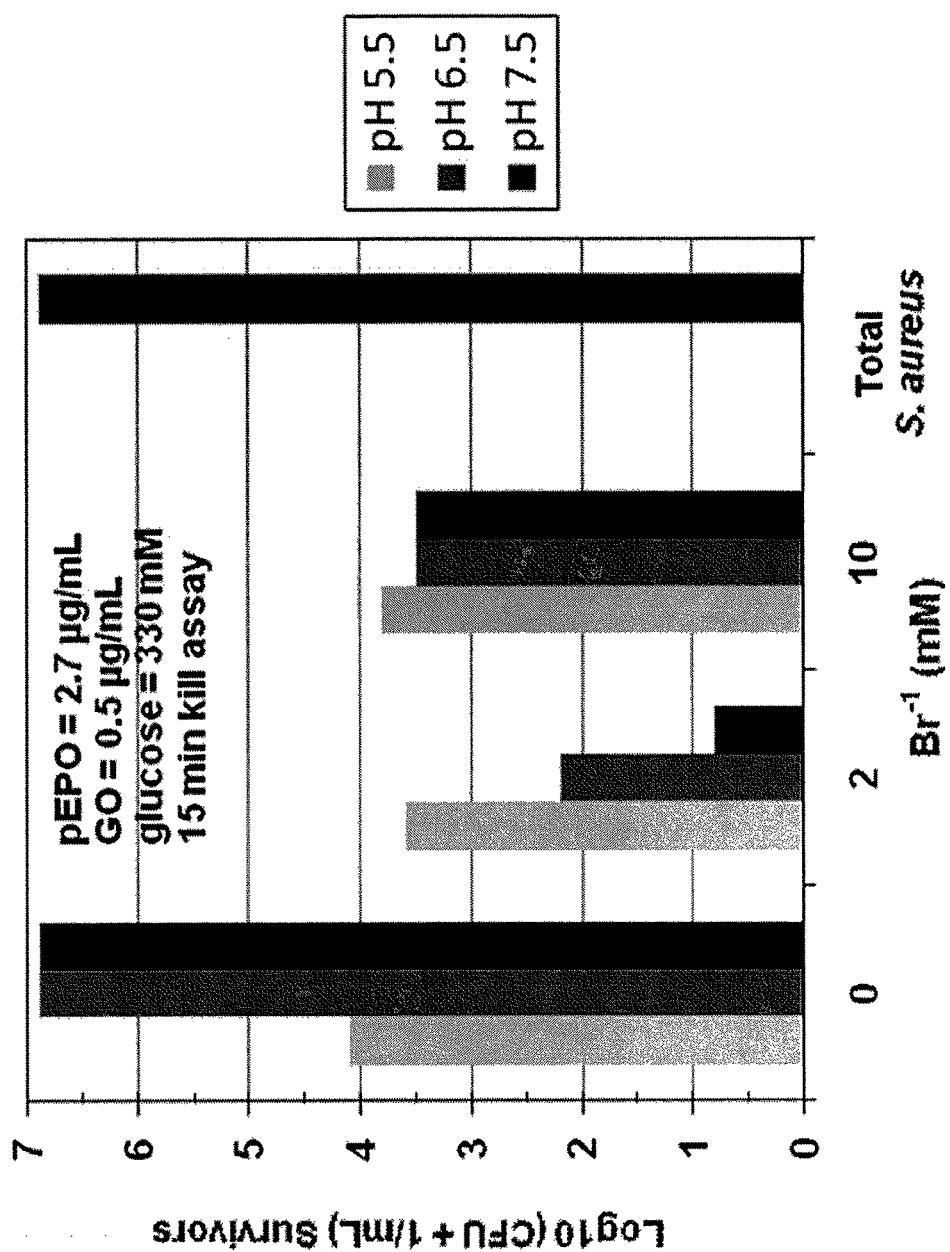
FIG. 6 is a graph comparing S. aureus kill as a function pH (5.5, 6.5, and 7.5) and bromide concentration (0, 2, 10 mM) for an eosinophil peroxidase (p-EPO) composition (p-EPO 2.7 µg/mL, GO 0.5 µg/mL, glucose 330 mM, 15 min assay).
Figure 7:
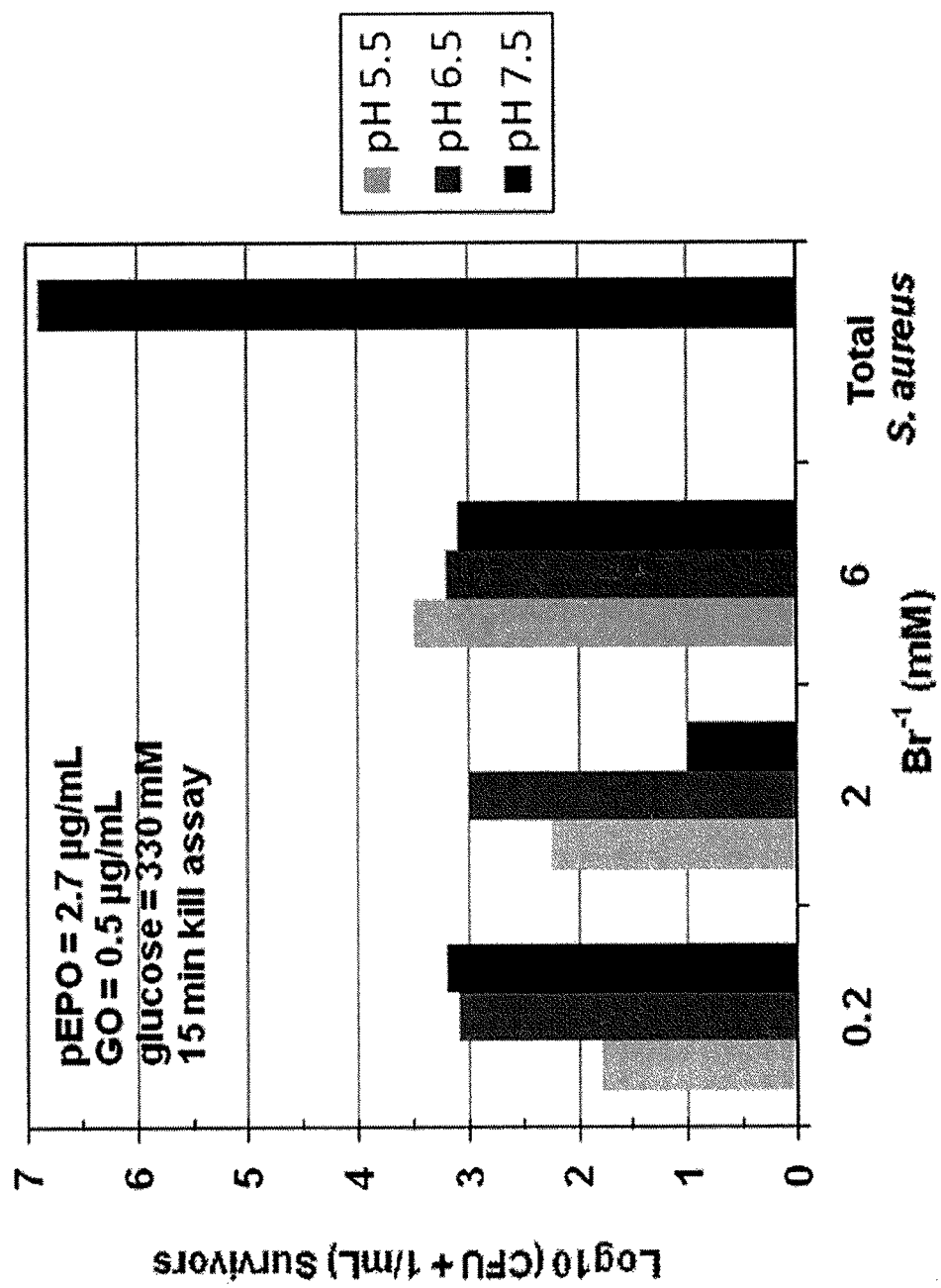
FIG. 7 is a graph comparing S. aureus kill as a function pH (5.5, 6.5, and 7.5) and bromide concentration (0.2, 2, 6 mM) for an eosinophil peroxidase (p-EPO) composition (p-EPO 2.7 µg/mL, GO 0.5 µg/mL, glucose 330 mM, 15 min assay).
Figure 8:
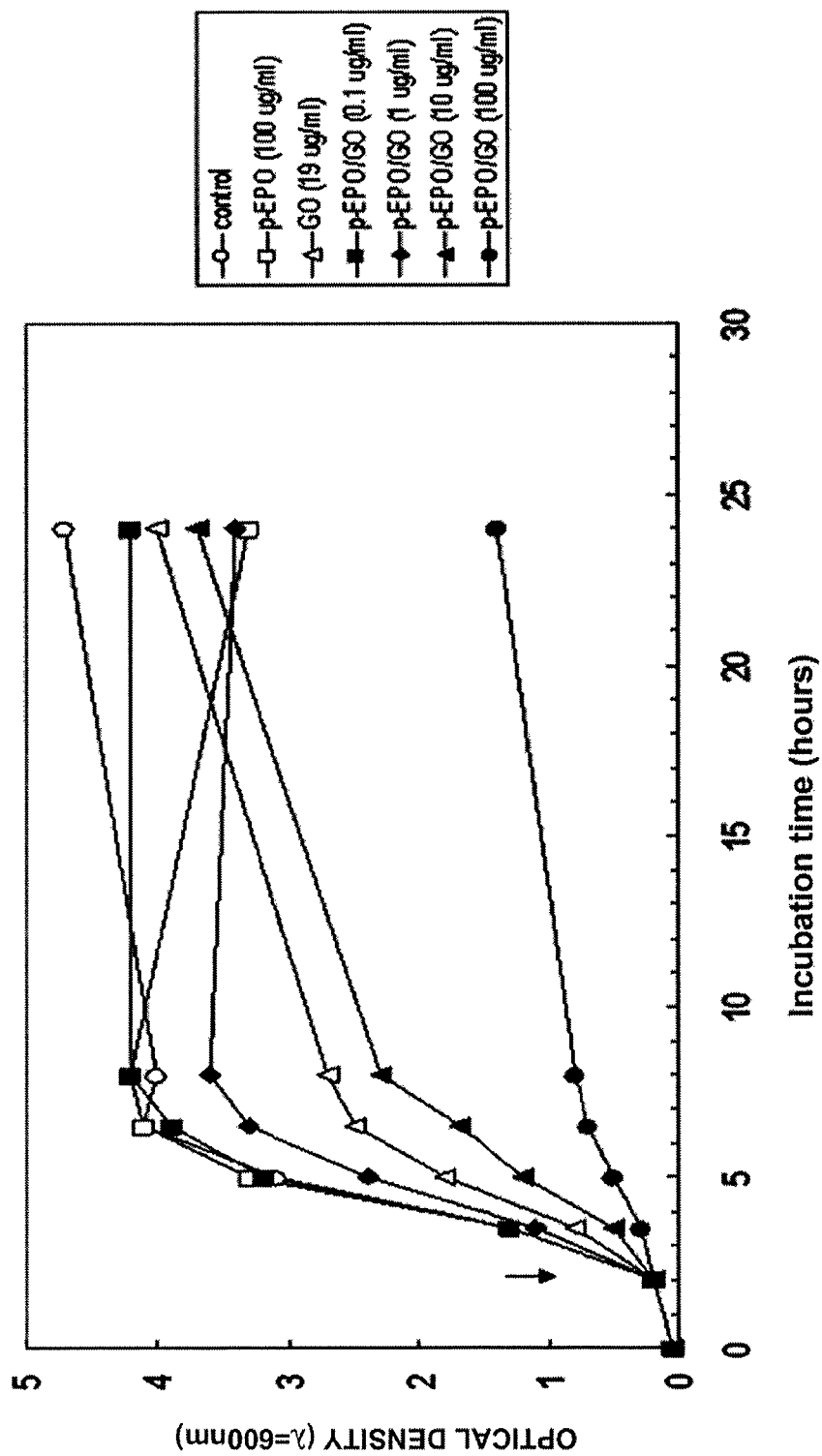
FIG. 8 is a graph comparing growth kinetics of S. aureus in tryptic soy broth (37° C.) for controls and p-EPO/GO compositions (0.1 mM KBr) as a function of incubation time (0-24 hours).

In this assay, kill was observed at each pH examined when bromide concentration was 2 mM (FIG. 6). Consistent with the earlier observation using N-bromotaurine formation (FIG. 1), added bromide was not critical when the pH was 5.5. However, at pH ≥6.5 no kill was observed in the absence of added bromide (FIG. 6).

pH v. Bromide Concentration

Repeat of study above (FIG. 6), but with bromide added at 0.2, 2.0, and 6 mM. Taken together, these data suggest that provided bromide is within the range of 0.2-10 mM, its absolute concentration is not critical. However, as pH values approach neutrality or higher, safer to maintain bromide at ≥2 mM.

Growth Kinetics of *S. aureus* in Tryptic Soy Broth (TSB)

Aliquots (10 μL each) of a fresh overnight *S. aureus* culture were used to inoculate 7 tubes each containing 0.5 mL of tryptic soy broth (37° C.) containing 0.1 mM KBr. Tubes were incubated (37° C.) for 2 hours, after which p-EPO (100 μg/mL final), GO (19 μg/mL final), or p-EPO/GO (100/19, w/w) was added (arrow in FIG. 8) at concentrations of 0.1; 1, 10, 100 μg/mL (reported as final p-EPO concentration). Growth of *S. aureus* was monitored by optical density measurements at λ=600 nm. Evident by FIG. 8, increasing concentrations of p-EPO/GO (≥1 μg/mL) slowed the growth of *S. aureus*. Glucose oxidase (19 μg/mL) alone slowed *S. aureus* growth. This was also the GO concentration of the p-EPO/GO (100 ng/mL) dose and thus demonstrates the added effect of p-EPO (compare open triangles, GO alone, with closed circles, p-EPO/GO).

Figure 9:
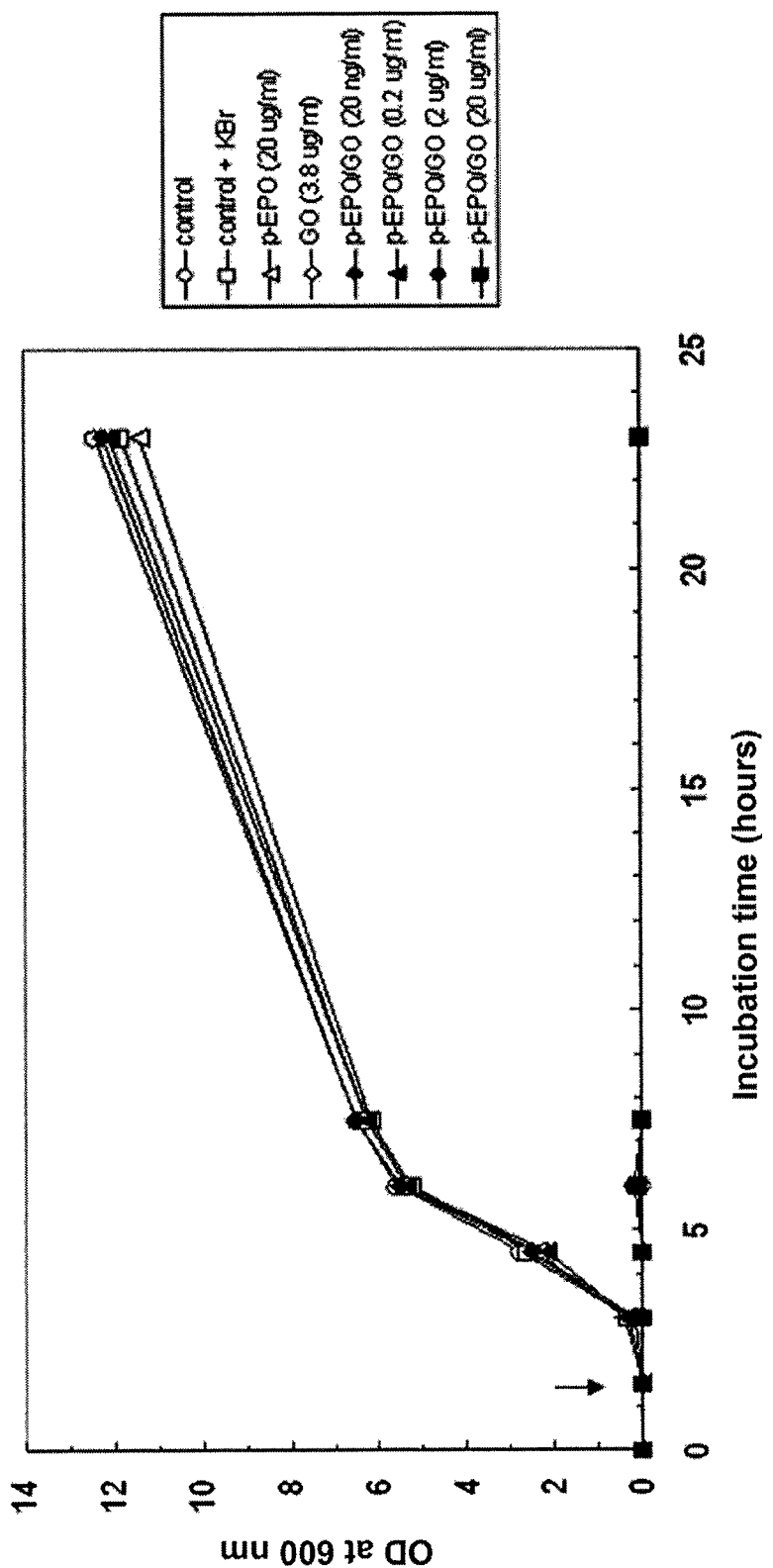
FIG. 9 is a graph comparing growth kinetics of S. aureus in tryptic soy broth (37° C.) for controls and p-EPO/GO compositions (1.0 mM KBr) as a function of incubation time (0-24 hours).

In a second study, an aliquot (10 μL each) of a fresh overnight *S. aureus* culture was used to inoculate eight tubes, each containing 0.5 mL of tryptic soy broth (37° C.) and seven of which also contained 1.0 mM KBr. Tubes were incubated (37° C.) for 1.5 hours, after which p-EPO (20 ng/mL final), GO (3.8 ng/mL final), or p-EPO/GO (100/19, w/w) was added (arrow) at concentrations of 0.02, 0.2, 2, 20 μg/mL (reported as final p-EPO concentration). Growth of *S. aureus* was measured by optical density at λ=600 nm. At this higher bromide concentration, p-EPO/GO (≥0.2 ng/mL) completely blocked *S. aureus* growth (FIG. 9). These studies demonstrated that at sufficient bromide concentration p-EPO/GO was able to block viability in a complex media at neutral pH (TSB pH about 7.4). Glucose concentration in TSB about 30 mM.

Bioactivity of p-EPO/GO in the Presence of Media Used for the Culture of Mammalian Cells Assays were performed as described above, except that Substrate Solution was diluted with William's E (WE) or Eagle's Minimum Essential (EMEM) media. Substrate Solution (pH 7.5) was 11 mM glucose, 2 mM KBr. Final p-EPO concentration was 2.7 ng/mL. Kill assay was 15 minutes at room temperature.

Figure 10:
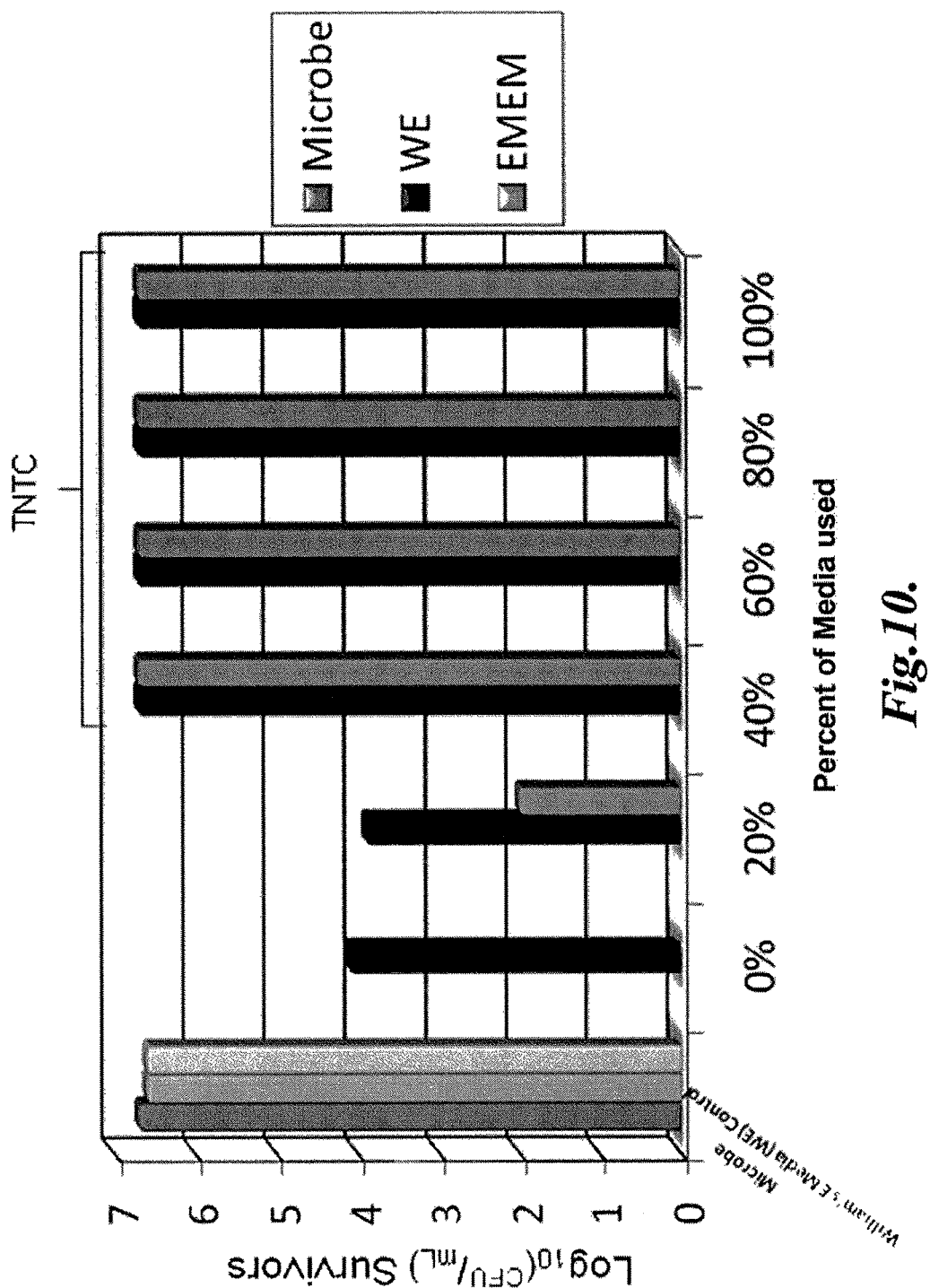
FIG. 10 is a graph comparing bioactivity of p-EPO/GO in a S. aureus kill assay as a function of percent (0, 20, 40, 60, 80, 100%) media (William's E, WE; Eagle's Minimum Essential Media, EMEM).

As shown in FIG. 10, potency was lost when culture media was mixed with the Substrate Solution at 40-100% culture media. In FIG. 10, 0% represents Substrate Solution only.

Example 3

Comparative In Vitro Activity of a Representative Eosinophil Peroxidase Formulation (C-101) and a Myeloperoxidase Formulation (E-101) Against Clinical Isolates of Target Pathogens In this example, the in vitro activity of a representative eosinophil peroxidase formulation of the invention (C-101) against clinical isolates of target pathogens is compared to a similarly constituted myeloperoxidase formulation (E-101).

Based on $MIC_{90}$ (minimum inhibitory concentration) and distribution data, the in vitro activities of E-101 and C-101 were highly comparable for all organisms studied (see Tables 1 and 2). The high level of comparability between both formulations was also reflected by scatterplot analysis whereby the MICs for E-101 and C-101 were analyzed head to head for each strain. With exception of nine isolates, the E-101 and C-101 MICs were the same against every strain tested. The breakout of strains for which MIC differences were encountered were as follows: (a) seven strains had C-101 MICs that were one doubling dilution lower than the E-101 MICs, these strains were comprised of one strain each of S. aureus, E. faecalis, E. coli, and four strains of P. aeruginosa; and (b) two strains (both K. pneumoniae) had E-101 MICs that were one doubling dilution lower than the C-101 MICs.

C-101 and E-101 Formulations.

Stock C-101 enzyme solution: 2.4 mg/mL porcine-eosinophil peroxidase (pEPO), 0.5 mg/mL GO in 20 mM Na phosphate, pH 6.5, 150 mM NaCl, 2 mM NaBr, 16.8 mM L-alanine, 21.6 mM L-proline, 21.6 mM glycine, 0.02% Tween-80. Stock C-101 substrate solution: 20 mM Na phosphate, pH 6.5, 150 mM NaCl, 2 mM NaBr, 0.02% Tween-80, and glucose (300 mM final).

Stock E-101 enzyme solution: 2.4 mg/mL porcine-myeloperoxidase (pMPO), 0.5 mg/mL GO in 20 mM Na phosphate, pH 6.5, 150 mM NaCl, 16.8 mM L-alanine, 21.6 mM L-proline, 21.6 mM glycine, 0.02% Tween-80. Stock E-101 substrate solution: 20 mM Na phosphate, pH 6.5, 150 mM NaCl, 0.02% Tween-80, and glucose (300 mM final).

Doubling dilutions were prepared for MIC testing ranging from 0.0008 to 8.0 µg/mL peroxidase.

Organisms.

Recent (2010-2011) non-duplicate, non-consecutive clinical isolates were evaluated. Isolates were selected at random from an unbiased surveillance collection so as to be representative of the population at large based on the below volume of isolates.

| Organism | Isolates Collected |
|---|---|
| S. aureus | 30 |
| E. coli | 30 |
| E. faecalis and E. faecium | 30 |
| K. pneumoniae | 30 |
| P. aeruginosa | 30 |
| TOTAL | 150 |

A summary of the isolates evaluated is provided in Appendix 1.

Methods.

All isolates were tested via broth microdilution according to CLSI defined methodology (Clinical and Laboratory Standards Institute. Methods for Dilution Antimicrobial Susceptibility Tests for Bacteria that Grow Aerobically; Approved Standard-$9^{th}$ ed. CLSI Document M7-A9. CLSI, Wayne, Pa. January 2012). Panels were made according to TSOP.MICRO.0135.US, Method B ("Panel preparation with serial dilutions performed in tubes") (Eurofins Medinet, Inc. EMI.0135. Method B. Preparation of Microbroth Dilution Panels. Revision 1. Chantilly, Va. Approved March 2010). Panels were made with 2× appropriate broth and 2× drug concentration and used on the same day without freezing. MIC testing was performed according TSOP.MICRO.0031.US (Eurofins Medinet, Inc. EMI.0031. Method B. Broth Microdilution MIC Testing with Frozen Panels. Revision 1. Chantilly, Va. Approved Quality Control (QC).

MIC testing of E-101 and C-101 was performed according to TSOP.MICRO.0031.US at a range of 8.0-0.008 µg/mL. QC Strains included ATCC 29213 S. aureus (0.01-0.03 mg pMPO/L) and ATCC 25922 E. coli (0.15-0.5 mg pMPO/L). See Appendix 2.

Results for all MIC testing were within the acceptable standards based on the CLSI recommended QC ranges for the appropriate ATCC control strains on each day of testing. Colony counts were performed on all QC isolates according to CLSI defined methodology.

The results are set forth below in Tables 1, 2a, and 2b

TABLE 1

MIC (mg pMPO/L) Profile of Clinical Isolates Evaluated Against E-101 and C-101.

| Organism | Drug | Total | Range | Mode | $MIC_{50}$ | $MIC_{90}$ |
|---|---|---|---|---|---|---|
| S. aureus | E-101 | 30 | ≤0.008-0.015 | 0.015 | 0.015 | 0.015 |
|  | C-101 | 30 | ≤0.008-0.015 | 0.015 | ≤0.008 | 0.015 |
| MRSA | E-101 | 25 | ≤0.008-0.015 | 0.015 | 0.015 | 0.015 |
|  | C-101 | 25 | ≤0.008-0.015 | 0.015 | 0.015 | 0.015 |
| MSSA | E-101 | 5 | ≤0.008-0.015 | ≤0.008 | NA[1] | NA |
|  | C-101 | 5 | ≤0.008-0.015 | ≤0.008 | NA | NA |
| E. faecalis | E-101 | 15 | 0.12-0.25 | 0.25 | 0.25 | 0.25 |
|  | C-101 | 15 | 0.06-0.25 | 0.25 | 0.25 | 0.25 |
| E. faecium | E-101 | 15 | 0.06-0.25 | 0.06 | 0.06 | 0.12 |
|  | C-101 | 15 | 0.06-0.25 | 0.06 | 0.06 | 0.12 |
| E. coli | E-101 | 30 | 0.015-0.25 | 0.12 | 0.12 | 0.25 |
|  | C-101 | 30 | 0.015-0.25 | 0.12 | 0.12 | 0.25 |

TABLE 1-continued

MIC (mg pMPO/L) Profile of Clinical Isolates Evaluated Against E-101 and C-101.

| Organism | Drug | Total | Range | Mode | $MIC_{50}$ | $MIC_{90}$ |
|---|---|---|---|---|---|---|
| MDR | E-101 | 8 | 0.12-0.25 | 0.12 | NA | NA |
| | C-101 | 8 | 0.12-0.25 | 0.12 | NA | NA |
| K. pneumoniae | E-101 | 30 | 0.06-0.25 | 0.12 | 0.12 | 0.25 |
| | C-101 | 30 | 0.06-0.25 | 0.12 | 0.12 | 0.25 |
| P. aeruginosa | E-101 | 30 | 0.015-0.25 | 0.06 | 0.06 | 0.12 |
| | C-101 | 30 | 0.015-0.12 | 0.06 | 0.06 | 0.12 |

[1]$MIC_{50}/MIC_{90}$ cannot be calculated when n < 10

TABLE 2a

MIC (mg pMPO/L) Distribution of Clinical Isolates Evaluated Against C-101.

| Drug | Organism | | Total | ≤0.008 | 0.015 | 0.03 | 0.06 | 0.12 | 0.25 | ≥0.5 |
|---|---|---|---|---|---|---|---|---|---|---|
| C-101 | S. aureus | Total | 30 | 15 | 15 | | | | | |
| | | % | | 50.0 | 50.0 | | | | | |
| | | Cumulative % | | 50.0 | 100.0 | | | | | |
| | MRSA | Total | 25.0 | 11 | 14 | | | | | |
| | | % | | 44.0 | 56.0 | | | | | |
| | | Cumulative % | | 44.0 | 100.0 | | | | | |
| | MSSA | Total | 5.0 | 4 | 1 | | | | | |
| | | % | | 80.0 | 20.0 | | | | | |
| | | Cumulative % | | 80.0 | 100.0 | | | | | |
| | E. faecalis | Total | 15 | | | | | 1 | 14 | |
| | | % | | | | | | 6.7 | 93.3 | |
| | | Cumulative % | | | | | | 6.7 | 100.0 | |
| | E. faecium | Total | 15 | | | | | 12 | 2 | 1 |
| | | % | | | | | | 80.0 | 13.3 | 6.7 |
| | | Cumulative % | | | | | | 80.0 | 93.3 | 100.0 |
| | E. coli | Total | 30 | | 1 | | 1 | 20 | 8 | |
| | | % | | | 3.3 | | 3.3 | 66.7 | 26.7 | |
| | | Cumulative % | | | 3.3 | | 6.7 | 73.3 | 100.0 | |
| | MDR | Total | 8.0 | | | | | 7 | 1 | |
| | | % | | | | | | 87.5 | 12.5 | |
| | | Cumulative % | | | | | | 87.5 | 100.0 | |
| | K. pneumoniae | Total | 30 | | | | 1 | 19 | 10 | |
| | | % | | | | | 3.3 | 63.3 | 33.3 | |
| | | Cumulative % | | | | | 3.3 | 66.7 | 100.0 | |
| | P. aeruginosa | Total | 30 | | 1 | 9 | 13 | 7 | | |
| | | % | | | 3.3 | 30.0 | 43.3 | 23.3 | | |
| | | Cumulative % | | | 3.3 | 33.3 | 76.7 | 100.0 | | |

TABLE 2b

MIC (mg pMPO/L) Distribution of Clinical Isolates Evaluated Against E-101.1

| Drug | Organism | | Total | ≤0.008 | 0.015 | 0.03 | 0.06 | 0.12 | 0.25 | ≥0.5 |
|---|---|---|---|---|---|---|---|---|---|---|
| E-101 | S. aureus | Total | 30 | 14 | 16 | | | | | |
| | | % | 100.0 | 46.7 | 53.3 | | | | | |
| | | Cumulative % | 100.0 | 463 | 100.0 | | | | | |
| | MRSA | Total | 25.0 | 11 | 14 | | | | | |
| | | % | 100.0 | 44.0 | 56.0 | | | | | |
| | | Cumulative % | 100.0 | 44.0 | 100.0 | | | | | |
| | MSSA | Total | 5.0 | 4 | 1 | | | | | |
| | | % | 100.0 | 80.0 | 20.0 | | | | | |
| | | Cumulative % | 100.0 | 80.0 | 100.0 | | | | | |
| | E. faecalis | Total | 15 | | | | | 1 | 14 | |
| | | % | 100.0 | | | | | 6.7 | 93.3 | |
| | | Cumulative % | 100.0 | | | | | 6.7 | 100.0 | |
| | E. faecium | Total | 15 | | | | | 12 | 2 | 1 |
| | | % | 100.0 | | | | | 80.0 | 13.3 | 6.7 |
| | | Cumulative % | 100.0 | | | | | 80.0 | 93.3 | 100.0 |
| | E. coli | Total | 30 | | 1 | | 1 | 19 | 9 | |
| | | % | 100.0 | | 3.3 | | 3.3 | 63.3 | 30.0 | |
| | | Cumulative % | 100.0 | | 3.3 | | 6.7 | 70.0 | 100.0 | |

TABLE 2b-continued

MIC (mg pMPO/L) Distribution of Clinical Isolates Evaluated Against E-101.1

| Drug | Organism | | Total | ≤0.008 | 0.015 | 0.03 | 0.06 | 0.12 | 0.25 | ≥0.5 |
|---|---|---|---|---|---|---|---|---|---|---|
| | MDR | Total | 8.0 | | | | | 6 | 2 | |
| | | % | 100.0 | | | | | 75.0 | 25.0 | |
| | | Cumulative % | 100.0 | | | | | 75.0 | 100.0 | |
| | K. pneumoniae | Total | 30 | | | | 1 | 21 | 8 | |
| | | % | 100.0 | | | | 3.3 | 70.0 | 26.7 | |
| | | Cumulative % | 100.0 | | | | 3.3 | 73.3 | 100.0 | |
| | P. aeruginosa | Total | 30 | | 1 | 7 | 14 | 7 | 1 | |
| | | % | 100.0 | | 3.3 | 23.3 | 46.7 | 23.3 | 3.3 | |
| | | Cumulative % | 100.0 | | 3.3 | 26.7 | 73.3 | 96.7 | 100.0 | |

APPENDIX 1

MIC (mg pMPO/L) Data for Isolates Evaluated Against C-101 and E-101.

| Organism | Eurofins ID | Phenotype | Source | County | Date Isolated | Age | Gender | MIC (C-101) | MIC (E-101) |
|---|---|---|---|---|---|---|---|---|---|
| S. aureus | 2849261 | MS | Unknown | US | 2011 | 47 | Female | ≤0.008 | 0.015 |
| S. aureus | 2821366 | MR | Wound | US | 2011 | 15 | Female | ≤0.008 | ≤0.008 |
| S. aureus | 2822028 | MR | Tissue | US | 2011 | 2 | Female | ≤0.008 | ≤0.008 |
| S. aureus | 2821338 | MS | Wound | US | 2011 | 37 | Male | ≤0.008 | ≤0.008 |
| S. aureus | 2822281 | MR | Wound | US | 2011 | 35 | Female | ≤0.008 | ≤0.008 |
| S. aureus | 2822846 | MR | Blood | US | 2011 | 86 | Male | ≤0.008 | ≤0.008 |
| S. aureus | 2823012 | MR | Unknown | US | 2011 | 47 | Female | ≤0.008 | ≤0.008 |
| S. aureus | 2823083 | MR | Sputum | US | 2011 | 70 | Male | ≤0.008 | ≤0.008 |
| S. aureus | 2857958 | MR | Urine | US | 2011 | 77 | Female | ≤0.008 | ≤0.008 |
| S. aureus | 2857963 | MR | Urine | US | 2011 | 51 | Female | ≤0.008 | ≤0.008 |
| S. aureus | 2878035 | MR | Wound | US | 2011 | 83 | Female | ≤0.008 | ≤0.008 |
| S. aureus | 2878137 | MR | Blood | US | 2011 | 80 | Male | ≤0.008 | ≤0.008 |
| S. aureus | 2879118 | MR | Tracheal Aspirate | US | 2011 | 52 | Female | ≤0.008 | ≤0.008 |
| S. aureus | 2821755 | MR | Wound | US | 2011 | 16 | Female | 0.015 | 0.015 |
| S. aureus | 2821811 | MR | Wound | US | 2011 | 70 | Female | 0.015 | 0.015 |
| S. aureus | 2822340 | MR | Skin | US | 2011 | 22 | Female | 0.015 | 0.015 |
| S. aureus | 2822282 | MS | Wound | US | 2011 | 42 | Male | ≤0.008 | ≤0.008 |
| S. aureus | 2823124 | MR | Wound | US | 2011 | 40 | Male | 0.015 | 0.015 |
| S. aureus | 2823171 | MR | Other | US | 2011 | 75 | Female | 0.015 | 0.015 |
| S. aureus | 2823214 | MR | Wound | US | 2011 | 21 | Female | 0.015 | 0.015 |
| S. aureus | 2822610 | MS | Other | US | 2011 | 49 | Male | ≤0.008 | ≤0.008 |
| S. aureus | 2822009 | MS | Wound | US | 2011 | 34 | Male | 0.015 | 0.015 |
| S. aureus | 2823473 | MR | Tissue | US | 2011 | 57 | Male | 0.015 | 0.015 |
| S. aureus | 2849259 | MR | Other | US | 2011 | 50 | Male | 0.015 | 0.015 |
| S. aureus | 2849283 | MR | Wound | US | 2011 | 25 | Female | 0.015 | 0.015 |
| S. aureus | 2850545 | MR | Sputum | US | 2011 | 53 | Male | 0.015 | 0.015 |
| S. aureus | 2850741 | MR | Skin | US | 2011 | 47 | Female | 0.015 | 0.015 |
| S. aureus | 2850816 | MR | NTN[1] | US | 2011 | 90 | Male | 0.015 | 0.015 |
| S. aureus | 2878130 | MR | Respiratory Tract | US | 2011 | 62 | Female | 0.015 | 0.015 |
| S. aureus | 2879665 | MR | Wound | US | 2011 | 40 | Male | 0.015 | 0.015 |
| E. faecalis | 2805411 | random | Blood | US | 2011 | 69 | Male | 0.25 | 0.25 |
| E. faecalis | 2805412 | random | Blood | US | 2011 | 44 | Female | 0.25 | 0.25 |
| E. faecalis | 2805413 | random | Blood | US | 2011 | 1 | Female | 0.25 | 0.25 |
| E. faecalis | 2805416 | random | Blood | US | 2011 | 38 | Male | 0.25 | 0.25 |
| E. faecalis | 2805419 | random | Blood | US | 2011 | 66 | Female | 0.06 | 0.06 |
| E. faecalis | 2805420 | random | Blood | US | 2011 | 68 | Female | 0.06 | 0.06 |
| E. faecalis | 2805484 | VRE | Urine | US | 2011 | 77 | Female | 0.06 | 0.12 |
| E. faecalis | 2805485 | random | Blood | US | 2011 | 83 | Female | 0.25 | 0.25 |
| E. faecalis | 2805486 | random | Urine | US | 2011 | 61 | Female | 0.25 | 0.25 |
| E. faecalis | 2805487 | random | Blood | US | 2011 | 42 | Male | 0.25 | 0.25 |
| E. faecalis | 2805488 | VRE | Urine | US | 2011 | 45 | Female | 0.25 | 0.25 |
| E. faecalis | 2805521 | random | Urine | US | 2011 | 76 | Female | 0.25 | 0.25 |
| E. faecalis | 2805522 | random | Other | US | 2011 | 65 | Female | 0.25 | 0.25 |
| E. faecalis | 2805523 | random | Blood | US | 2011 | 49 | Female | 0.25 | 0.25 |
| E. faecalis | 2805524 | random | Urine | US | 2011 | 66 | Female | 0.25 | 0.25 |
| E. faecium | 2805414 | VRE | Blood | US | 2011 | 63 | Male | 0.06 | 0.06 |
| E. faecium | 2805415 | VRE | Blood | US | 2011 | 63 | Male | 0.06 | 0.06 |
| E. faecium | 2805417 | VRE | Blood | US | 2011 | 56 | Female | 0.06 | 0.06 |
| E. faecium | 2805418 | VRE | Blood | US | 2011 | 90 | Female | 0.06 | 0.06 |
| E. faecium | 2805483 | random | Blood | US | 2011 | 85 | Female | 0.25 | 0.25 |
| E. faecium | 2805519 | VRE | Urine | US | 2011 | 87 | Female | 0.25 | 0.25 |
| E. faecium | 2805520 | random | Urine | US | 2011 | 82 | Male | 0.25 | 0.25 |
| E. faecium | 2805633 | random | Blood | US | 2011 | 82 | Male | 0.06 | 0.06 |
| E. faecium | 2805634 | VRE | Blood | US | 2011 | 84 | Male | 0.06 | 0.06 |
| E. faecium | 2805666 | random | Blood | US | 2011 | 50 | Male | 0.06 | 0.06 |

APPENDIX 1-continued

MIC (mg pMPO/L) Data for Isolates Evaluated Against C-101 and E-101.

| Organism | Eurofins ID | Phenotype | Source | County | Date Isolated | Age | Gender | MIC (C-101) | MIC (E-101) |
|---|---|---|---|---|---|---|---|---|---|
| E. faecium | 2805669 | random | Urine | US | 2011 | 74 | Male | 0.12 | 0.12 |
| E. faecium | 2805670 | VRE | Wound | US | 2011 | 42 | Male | 0.06 | 0.06 |
| E. faecium | 2805773 | random | Urine | US | 2011 | 74 | Male | 0.12 | 0.12 |
| E. faecium | 2805777 | random | Wound | US | 2011 | 90 | Female | 0.06 | 0.06 |
| E. faecium | 2806239 | random | Other | US | 2011 | 90 | Female | 0.06 | 0.06 |
| E. coli | 2691995 | random | Sputum | US | 2011 | 88 | Female | 0.25 | 0.25 |
| E. coli | 2691997 | random | Sputum | US | 2011 | 45 | Male | 0.25 | 0.25 |
| E. coli | 2692298 | random | Blood | US | 2011 | 68 | Male | 0.12 | 0.12 |
| E. coli | 2692380 | random | Urine | US | 2011 | 55 | Unknown | 0.12 | 0.12 |
| E. coli | 2692382 | random | Urine | US | 2011 | 42 | Male | 0.25 | 0.25 |
| E. coli | 2692383 | random | Other | US | 2011 | 59 | Female | 0.25 | 0.25 |
| E. coli | 2692384 | random | Urine | US | 2011 | 66 | Female | 0.12 | 0.12 |
| E. coli | 2692386 | random | Urine | US | 2011 | 45 | Female | 0.06 | 0.06 |
| E. coli | 2692593 | random | Blood | US | 2011 | 51 | Male | 0.015 | 0.015 |
| E. coli | 2692596 | random | Blood | US | 2011 | 31 | Female | 0.25 | 0.25 |
| E. coli | 2692597 | random | Blood | US | 2011 | 64 | Male | 0.12 | 0.12 |
| E. coil | 2692598 | random | Wound | US | 2011 | 69 | Male | 0.25 | 0.25 |
| E. coli | 2692599 | random | Blood | US | 2011 | 89 | Male | 0.25 | 0.25 |
| E. coli | 2692680 | random | Urine | US | 2011 | 68 | Male | 0.12 | 0.12 |
| E. coli | 2692687 | random | Respiratory Tract | US | 2011 | 69 | Male | 0.12 | 0.12 |
| E. coil | 2692689 | random | Other | US | 2011 | 70 | Female | 0.12 | 0.12 |
| E. coli | 2692883 | random | Urine | US | 2011 | 59 | Female | 0.12 | 0.12 |
| E. coli | 2692978 | random | Wound | US | 2011 | 58 | Male | 0.12 | 0.12 |
| E. coli | 2693449 | random | Unknown | US | 2011 | Unknown | Unknown | 0.12 | 0.12 |
| E. coli | 2693518 | random | Blood | US | 2011 | 54 | Male | 0.12 | 0.12 |
| E. coli | 2740313 | random | Wound | US | 2011 | 84 | Female | 0.12 | 0.12 |
| E. coli | 2740317 | random | Other | US | 2011 | 79 | Female | 0.12 | 0.12 |
| E. coli | 2802771 | MDR | Wound | US | 2011 | 61 | Female | 0.12 | 0.12 |
| E. coli | 2810666 | MDR | Blood | US | 2011 | 64 | Female | 0.12 | 0.12 |
| E. coli | 2811301 | MDR | Blood | US | 2011 | 50 | Male | 0.12 | 0.12 |
| E. coli | 2820723 | MDR | Tracheal As pirate | US | 2011 | 57 | Male | 0.12 | 0.12 |
| E. coli | 2820724 | MDR | Tracheal As pirate | US | 2011 | 51 | Male | 0.12 | 0.12 |
| E. coli | 2833067 | MDR | Urine | US | 2011 | 86 | Male | 0.12 | 0.12 |
| E. coli | 2807865 | MDR | Blood | US | 2011 | 71 | Male | 0.12 | 0.25 |
| E. coli | 2807871 | MDR | Sputum | US | 2011 | 68 | Male | 0.25 | 0.25 |
| K. pneumoniae | 2801983 | CAZ-R | Wound | US | 2011 | 45 | Male | 0.25 | 0.25 |
| K. pneumoniae | 2802146 | random | Skin | US | 2011 | 28 | Female | 0.12 | 0.12 |
| K. pneumoniae | 2802310 | random | Blood | US | 2011 | 57 | Male | 0.25 | 0.25 |
| K. pneumoniae | 2802549 | random | Sputum | US | 2011 | 54 | Female | 0.12 | 0.12 |
| K. pneumoniae | 2802619 | random | Blood | US | 2011 | 39 | Male | 0.12 | 0.12 |
| K. pneumoniae | 2802620 | random | Urine | US | 2011 | 74 | Female | 0.12 | 0.12 |
| K. pneumoniae | 2802778 | CAZ-R | Urine | US | 2011 | 70 | Male | 0.12 | 0.12 |
| K. pneumoniae | 2802782 | random | Blood | US | 2011 | 17 | Male | 0.12 | 0.12 |
| K. pneumoniae | 2802946 | random | Unknown | US | 2011 | 90 | Female | 0.12 | 0.12 |
| K. pneumoniae | 2804366 | random | Urine | US | 2011 | 88 | Female | 0.12 | 0.12 |
| K. pneumoniae | 2804531 | random | Sputum | US | 2011 | 71 | Female | 0.25 | 0.25 |
| K. pneumoniae | 2804848 | random | BAL | US | 2011 | 64 | Male | 0.25 | 0.25 |
| K. pneumoniae | 2804852 | random | Sputum | US | 2011 | 74 | Male | 0.25 | 0.25 |
| K. pneumoniae | 2808669 | random | Wound | US | 2011 | 86 | Female | 0.25 | 0.25 |
| K. pneumoniae | 2810122 | random | Other | US | 2011 | 30 | Female | 0.12 | 0.12 |
| K. pneumoniae | 2810675 | random | Blood | US | 2011 | 63 | Female | 0.12 | 0.12 |
| K. pneumoniae | 2810762 | random | Blood | US | 2011 | 70 | Female | 0.12 | 0.12 |
| K. pneumoniae | 2810912 | CAZ-R | Wound | US | 2011 | 66 | Male | 0.12 | 0.12 |
| K. pneumoniae | 2810922 | random | Blood | US | 2011 | 75 | Male | 0.12 | 0.12 |
| K. pneumoniae | 2811317 | random | Blood | US | 2011 | Unknown | Unknown | 0.12 | 0.12 |
| K. pneumoniae | 2812057 | random | Blood | US | 2011 | 40 | Female | 0.12 | 0.12 |
| K. pneumoniae | 2812295 | random | Blood | US | 2011 | 80 | Male | 0.25 | 0.25 |
| K. pneumoniae | 2819965 | random | Wound | US | 2011 | 49 | Male | 0.06 | 0.06 |
| K. pneumoniae | 2820739 | CAZ-R | Blood | US | 2011 | 74 | Male | 0.12 | 0.12 |
| K. pneumoniae | 2824058 | random | Blood | US | 2011 | Unknown | Male | 0.25 | 0.25 |
| K. pneumoniae | 2826406 | random | Other | US | 2011 | 52 | Female | 0.12 | 0.12 |
| K. pneumoniae | 2826484 | random | Sputum | US | 2011 | 64 | Male | 0.25 | 0.12 |
| K. pneumoniae | 2835637 | random | Wound | US | 2011 | 71 | Female | 0.12 | 0.12 |
| K. pneumoniae | 2835805 | random | Sputum | US | 2011 | 20 | Female | 0.25 | 0.12 |
| K. pneumoniae | 2845803 | random | Wound | US | 2011 | 53 | Male | 0.12 | 0.12 |
| P. aeruginosa | 2802165 | random | Skin | US | 2011 | 57 | Unknown | 0.06 | 0.06 |
| P. aeruginosa | 2802250 | random | Sputum | US | 2011 | 71 | Female | 0.06 | 0.06 |
| P. aeruginosa | 2802730 | random | Sputum | US | 2011 | Unknown | Female | 0.03 | 0.03 |
| P. aeruginosa | 2802734 | MDR | Other | US | 2011 | Unknown | Male | 0.03 | 0.03 |
| P. aeruginosa | 2802960 | random | Skin | US | 2011 | 76 | Male | 0.12 | 0.12 |
| P. aeruginosa | 2807832 | MDR | Wound | US | 2011 | 51 | Male | 0.015 | 0.015 |
| P. aeruginosa | 2807835 | MDR | Tracheal Aspirate | US | 2011 | 64 | Male | 0.03 | 0.06 |
| P. aeruginosa | 2807908 | random | Tracheal Aspirate | US | 2011 | 68 | Male | 0.03 | 0.03 |

APPENDIX 1-continued

MIC (mg pMPO/L) Data for Isolates Evaluated Against C-101 and E-101.

| Organism | Eurofins ID | Phenotype | Source | County | Date Isolated | Age | Gender | MIC (C-101) | MIC (E-101) |
|---|---|---|---|---|---|---|---|---|---|
| P. aeruginosa | 2808714 | random | Sputum | US | 2011 | 62 | Female | 0.03 | 0.03 |
| P. aeruginosa | 2810135 | MDR | Sputum | US | 2011 | 63 | Female | 0.12 | 0.25 |
| P. aeruginosa | 2810147 | random | Blood | US | 2011 | 85 | Female | 0.12 | 0.12 |
| P. aeruginosa | 2810148 | MDR | Wound | US | 2011 | 72 | Female | 0.06 | 0.06 |
| P. aeruginosa | 2810213 | random | Sputum | US | 2011 | 66 | Male | 0.06 | 0.06 |
| P. aeruginosa | 2810215 | random | Blood | US | 2011 | 67 | Male | 0.06 | 0.06 |
| P. aeruginosa | 2810379 | random | Wound | US | 2011 | 27 | Male | 0.12 | 0.12 |
| P. aeruginosa | 2811333 | random | Wound | US | 2011 | Unknown | Unknown | 0.06 | 0.06 |
| P. aeruginosa | 2812071 | random | Wound | US | 2011 | 65 | Male | 0.06 | 0.06 |
| P. aeruginosa | 2812074 | random | Wound | US | 2011 | 87 | Female | 0.06 | 0.06 |
| P. aeruginosa | 2812318 | random | Blood | US | 2011 | 54 | Female | 0.03 | 0.03 |
| P. aeruginosa | 2812775 | random | Wound | US | 2011 | 65 | Male | 0.06 | 0.06 |
| P. aeruginosa | 2819833 | random | Sputum | US | 2011 | 58 | Male | 0.03 | 0.06 |
| P. aeruginosa | 2820769 | MDR | Tracheal Aspirate | US | 2011 | 80 | Female | 0.06 | 0.06 |
| P. aeruginosa | 2823763 | random | Wound | US | 2011 | 81 | Female | 0.06 | 0.06 |
| P. aeruginosa | 2823771 | random | Wound | US | 2011 | 75 | Female | 0.12 | 0.12 |
| P. aeruginosa | 2824087 | random | Sputum | US | 2011 | 9 | Female | 0.03 | 0.03 |
| P. aeruginosa | 2826510 | random | Sputum | US | 2011 | 3 | Male | 0.03 | 0.03 |
| P. aeruginosa | 2826751 | random | BAL[2] | US | 2011 | 45 | Male | 0.12 | 0.12 |
| P. aeruginosa | 2828101 | random | Wound | US | 2011 | 60 | Male | 0.06 | 0.06 |
| P. aeruginosa | 2833102 | MDR | Wound | US | 2011 | 80 | Female | 0.06 | 0.12 |
| P. aeruginosa | 2833105 | MDR | Sputum | US | 2011 | 63 | Female | 0.12 | 0.12 |

[1]NTN = Nasopharynx/Throat/Nose
[2]BAL = Bronchial Alveolar Lavage

APPENDIX 2

QC Organism Colony Counts.
Appendix 2. QC Organism Colony Counts

| Organism | Initial Colony Count (CFU/mL) |
|---|---|
| S. aureus ATCC 29213 | $6.0 \times 10^5$ |
| E. faecalis ATCC 29212 | $5.5 \times 10^5$ |
| E. coli ATCC 25922 | $2.5 \times 10^5$ |
| K. pneumoniae ATCC 700603 | $6.0 \times 10^5$ |
| P. aeruginosa ATCC 27853 | $6.0 \times 10^5$ |

Example 4

Comparative Time Kill Studies for a Representative Eosinophil Peroxidase (C-101) Solution and a Myeloperoxidase (E-101) Solution Against Select Gram-Positive and Gram-Negative ATCC Organisms In this example, the time kill of a representative eosinophil peroxidase solution of the invention (C-101) against select gram-positive and gram-negative ATCC organisms is compared to a similarly constituted myeloperoxidase formulation (E-101).

C-101 and E-101 Formulations.

Stock C-101 enzyme solution: 2.4 mg/mL porcine-eosinophil peroxidase (pEPO), 0.5 mg/mL glucose oxidase (GO) in 20 mM Na phosphate, pH 6.5, 150 mM NaCl, 2 mM NaBr, 16.8 mM L-alanine, 21.6 mM L-proline, 21.6 mM glycine, 0.02% Tween-80. Stock C-101 substrate solution: 20 mM Na phosphate, pH 6.5, 150 mM NaCl, 2 mM NaBr, 0.02% Tween-80, and glucose (300 mM final).

Stock E-101 enzyme solution: 2.4 mg/mL porcine-myeloperoxidase (pMPO), 0.5 mg/mL GO in 20 mM Na phosphate, pH 6.5, 150 mM NaCl, 16.8 mM L-alanine, 21.6 mM L-proline, 21.6 mM glycine, 0.02% Tween-80. Stock E-101 substrate solution: 20 mM Na phosphate, pH 6.5, 150 mM NaCl, 0.02% Tween-80, and glucose (300 mM Doubling dilutions were prepared for MIC testing ranging from 0.0008 to 8.0 µg/mL peroxidase.

Organisms.

C-101 and E-101 solutions were tested against selected ATCC organisms S. aureus ATCC 29213, E. faecalis ATCC 29212, E. coli ATCC 25922, and P. aeruginosa ATCC 27853.

Methods.

All isolates were tested via the time kill method as specified by CLSI document M26-A (Clinical and Laboratory Standards Institute, Methods for Determining Bactericidal Activity of Antimicrobial Agents, Approved Guideline. CLSI, Wayne, Pa. January 2012). Panels were prepared on the same day that isolates were prepared in accordance with CLSI document M7 (Clinical and Laboratory Standards Institute, Methods for Dilution Antimicrobial Susceptibility Tests for Bacteria that Grow Anaerobically; Approved Standard-9th edition. CLSI, Wayne, Pa. January 2012). Data was record as a $Log_{10}$ reduction in CFU at designated time points compared to control counts.

Quality Control (QC).

Bacterial counts for controls (inocula with no compound) were recorded versus time (CLSI M100) (Clinical and Laboratory Standards Institute, Performance Standards for Antimicrobial Susceptibility Testing; Twentieth Informational Supplement. CLSI, Wayne, Pa. January 2012).

The summary data used to produce the time kill curves for each organism tested against C-101 and E-101 are provided in Tables 3 and 4, respectively.

TABLE 3

Time Kill Kinetics of C-101 Against Selected QC Organisms (CFU/mL).

| Organism | C-101 (μg/mL) | Time Point (Hours) | | | | | | |
|---|---|---|---|---|---|---|---|---|
| | | 0 | 0.03 | 0.26 | 0.5 | 1 | 4 | 24 |
| S. aureus 29213 | 0 | 2.20E+05 | 2.20E+05 | 2.60E+05 | 2.00E+05 | 2.00E+05 | 2.02E+07 | 6.20E+10 |
| | 0.06 | 2.20E+05 | 1.18E+05 | 1.20E+05 | 1.26E+05 | 1.26E+05 | 9.60E+02 | <2.00E+02 |
| | 0.25 | 2.20E+05 | 1.02E+05 | 8.60E+04 | 9.00E+04 | 7.20E+04 | 6.40E+02 | <2.00E+02 |
| | 1 | 2.20E+05 | 1.20E+05 | 1.18E+05 | 7.20E+04 | 6.20E+04 | <2.00E+02 | <2.00E+02 |
| | 4 | 2.20E+05 | 1.08E+05 | 1.00E+05 | 9.20E+04 | 8.20E+04 | 6.00E+02 | <2.00E+02 |
| | 16 | 2.20E+05 | 9.40E+04 | 1.06E+05 | 9.00E+04 | 7.00E+04 | <2.00E+02 | <2.00E+02 |
| | 64 | 2.20E+05 | <2.00E+02 | <2.00E+02 | <2.00E+02 | <2.00E+02 | <2.00E+02 | <2.00E+02 |
| | 256 | 2.20E+05 | <2.00E+02 | <2.00E+02 | <2.00E+02 | <2.00E+02 | <2.00E+02 | <2.00E+02 |
| E. coli 25922 | 0 | 1.30E+05 | 1.30E+05 | 1.18E+05 | 1.80E+05 | 2.00E+05 | 1.12E+07 | 1.48E+10 |
| | 0.06 | 1.30E+05 | 1.00E+05 | 1.16E+05 | 9.80E+04 | 1.10E+05 | 2.06E+04 | 1.00E+09 |
| | 0.25 | 1.30E+05 | 9.40E+04 | 7.20E+04 | 8.80E+04 | 7.80E+04 | <2.00E+02 | <2.00E+02 |
| | 1 | 1.30E+05 | 9.00E+04 | 8.80E+04 | 8.60E+04 | 3.20E+04 | <2.00E+02 | <2.00E+02 |
| | 4 | 1.30E+05 | 9.40E+04 | 8.60E+04 | 8.80E+04 | 4.00E+04 | <2.00E+02 | <2.00E+02 |
| | 16 | 1.30E+05 | 9.00E+04 | 9.40E+04 | 6.60E+04 | 7.40E+04 | <2.00E+02 | <2.00E+02 |
| | 64 | 1.30E+05 | <2.00E+02 | <2.00E+02 | <2.00E+02 | <2.00E+02 | <2.00E+02 | <2.00E+02 |
| | 256 | 1.30E+05 | <2.00E+02 | <2.00E+02 | <2.00E+02 | <2.00E+02 | <2.00E+02 | <2.00E+02 |
| E. faecalis 29212 | 0 | 2.80E+05 | 2.80E+05 | 3.00E+05 | 3.20E+05 | 5.60E+05 | 1.00E+08 | 1.58E+10 |
| | 0.06 | 2.80E+05 | 3.36E+05 | 3.18E+05 | 3.24E+05 | 5.20E+05 | 1.96E+07 | 1.38E+10 |
| | 0.25 | 2.80E+05 | 2.42E+05 | 1.84E+05 | 2.06E+05 | 4.60E+05 | 3.08E+06 | 1.12E+09 |
| | 1 | 2.80E+05 | 2.38E+05 | 2.80E+05 | 2.96E+05 | 3.68E+05 | 3.60E+05 | <2.00E+02 |
| | 4 | 2.80E+05 | 3.10E+05 | 2.78E+05 | 3.06E+05 | 3.32E+05 | 3.54E+05 | <2.00E+02 |
| | 16 | 2.80E+05 | 2.40E+05 | 2.16E+05 | 2.34E+05 | 3.24E+05 | <2.00E+02 | <2.00E+02 |
| | 64 | 2.80E+05 | 2.86E+05 | 2.82E+05 | 3.06E+05 | 2.60E+04 | <2.00E+02 | <2.00E+02 |
| | 256 | 2.80E+05 | 2.86E+05 | 2.26E+05 | 5.00E+04 | <2.00E+02 | <2.00E+02 | <2.00E+02 |
| P. aeruginosa 27853 | 0 | 1.72E+05 | 1.72E+05 | 1.58E+05 | 1.00E+05 | 8.20E+04 | 5.20E+06 | 2.80E+10 |
| | 0.06 | 1.72E+05 | 1.68E+05 | 1.74E+05 | 9.20E+04 | 9.80E+03 | <2.00E+02 | <2.00E+02 |
| | 0.25 | 1.72E+05 | 2.16E+05 | 1.32E+05 | 1.00E+05 | 9.80E+03 | <2.00E+02 | <2.00E+02 |
| | 1 | 1.72E+05 | 2.34E+05 | 1.62E+05 | 8.60E+04 | 2.80E+02 | <2.00E+02 | <2.00E+02 |
| | 4 | 1.72E+05 | 1.88E+05 | 1.24E+05 | 8.80E+04 | 1.40E+03 | <2.00E+02 | <2.00E+02 |
| | 16 | 1.72E+05 | 1.72E+05 | 1.24E+05 | 4.20E+04 | <2.00E+02 | <2.00E+02 | <2.00E+02 |
| | 64 | 1.72E+05 | 6.00E+02 | 6.00E+02 | 6.00E+02 | <2.00E+02 | <2.00E+02 | <2.00E+02 |
| | 256 | 1.72E+05 | 4.00E+02 | 4.00E+02 | <2.00E+02 | <2.00E+02 | <2.00E+02 | <2.00E+02 |

TABLE 4

Time Kill Kinetics of E-101 Against Selected QC Organisms (CFU/mL).

| Organism | E-101 (μg/mL) | Time Point (Hours) | | | | | | |
|---|---|---|---|---|---|---|---|---|
| | | 0 | 0.03 | 0.25 | 0.5 | 1 | 4 | 24 |
| S. aureus 29213 | 0 | 2.60E+05 | 2.60E+05 | 2.40E+05 | 2.20E+05 | 2.20E+05 | 2.98E+07 | 7.00E+10 |
| | 0.06 | 2.60E+05 | 1.26E+05 | 1.18E+05 | 1.14E+05 | 1.25E+05 | 6.00E+02 | <2.00E+02 |
| | 0.25 | 2.60E+05 | 1.46E+05 | 9.60E+04 | 9.20E+04 | 9.20E+04 | 6.80E+02 | <2.00E+02 |
| | 1 | 2.60E+05 | 1.20E+05 | 9.20E+04 | 6.80E+04 | 5.60E+04 | <2.00E+02 | <2.00E+02 |
| | 4 | 2.60E+05 | 9.00E+04 | 5.80E+04 | 8.20E+04 | 9.20E+04 | <2.00E+02 | <2.00E+02 |
| | 16 | 2.60E+05 | 8.80E+04 | 5.40E+04 | 7.40E+04 | 4.80E+04 | <2.00E+02 | <2.00E+02 |
| | 64 | 2.60E+05 | 8.80E+03 | 6.60E+03 | 4.60E+03 | 3.60E+03 | <2.00E+02 | <2.00E+02 |
| | 256 | 2.60E+05 | <2.00E+02 | <2.00E+02 | <2.00E+02 | <2.00E+02 | <2.00E+02 | <2.00E+02 |
| E. coli 25922 | 0 | 1.02E+05 | 1.02E+05 | 1.04E+05 | 1.40E+05 | 1.36E+05 | 8.00E+06 | 1.18E+10 |
| | 0.06 | 1.02E+05 | 1.02E+05 | 1.00E+05 | 1.14E+05 | 6.80E+04 | 3.00E+04 | 2.66E+08 |
| | 0.25 | 1.02E+05 | 1.04E+05 | 1.12E+05 | 8.00E+04 | 3.20E+04 | <2.00E+02 | <2.00E+02 |
| | 1 | 1.02E+05 | 1.06E+05 | 1.08E+05 | 8.80E+04 | 3.22E+04 | <2.00E+02 | <2.00E+02 |
| | 4 | 1.02E+05 | 1.08E+05 | 1.06E+05 | 8.60E+04 | 4.80E+04 | <2.00E+02 | <2.00E+02 |
| | 16 | 1.02E+05 | 1.00E+05 | 1.06E+05 | 1.02E+05 | 9.40E+04 | <2.00E+02 | <2.00E+02 |
| | 64 | 1.02E+05 | 8.80E+04 | 7.00E+04 | 5.60E+04 | 3.00E+03 | <2.00E+02 | <2.00E+02 |
| | 256 | 1.02E+05 | 1.80E+05 | 1.98E+05 | <2.00E+02 | <2.00E+02 | <2.00E+02 | <2.00E+02 |
| E. faecalis 29212 | 0 | 2.98E+05 | 2.98E+05 | 2.86E+05 | 2.94E+05 | 5.60E+05 | 1.16E+08 | 1.52E+10 |
| | 0.06 | 2.98E+05 | 3.46E+05 | 9.20E+05 | 3.16E+05 | 4.60E+05 | 1.76E+07 | 1.46E+10 |
| | 0.25 | 2.98E+05 | 2.50E+05 | 2.44E+05 | 3.46E+05 | 3.32E+05 | 3.38E+06 | 1.56E+10 |
| | 1 | 2.98E+05 | 2.64E+05 | 2.96E+05 | 3.20E+05 | 3.78E+05 | 8.80E+05 | <2.00E+02 |
| | 4 | 2.98E+05 | 2.92E+05 | 2.86E+05 | 2.98E+05 | 5.00E+05 | 4.80E+05 | <2.00E+02 |
| | 16 | 2.98E+05 | 3.08E+05 | 2.78E+05 | 2.70E+05 | 2.36E+05 | <2.00E+02 | <2.00E+02 |
| | 64 | 2.98E+05 | 2.50E+05 | 2.56E+05 | 2.92E+05 | 7.00E+04 | <2.00E+02 | <2.00E+02 |
| | 256 | 2.98E+05 | 2.58E+05 | 1.68E+05 | 1.68E+05 | <2.00E+02 | <2.00E+02 | <2.00E+02 |
| P. aeruginosa 27853 | 0 | 2.40E+05 | 2.40E+05 | 2.10E+05 | 2.00E+05 | 1.88E+05 | 1.34E+06 | 2.54E+10 |
| | 0.06 | 2.40E+05 | 1.94E+05 | 2.20E+05 | 1.92E+05 | 3.00E+05 | <2.00E+02 | <2.00E+02 |
| | 0.25 | 2.40E+05 | 2.00E+05 | 2.26E+05 | 1.44E+05 | 8.80E+03 | <2.00E+02 | <2.00E+02 |
| | 1 | 2.40E+05 | 2.00E+05 | 1.80E+05 | 1.46E+05 | 5.00E+03 | <2.00E+02 | <2.00E+02 |
| | 4 | 2.40E+05 | 2.02E+05 | 2.44E+05 | 1.34E+05 | 1.60E+03 | <2.00E+02 | <2.00E+02 |

TABLE 4-continued

Time Kill Kinetics of E-101 Against Selected QC Organisms (CFU/mL).

| Organism | E-101 (µg/mL) | Time Point (Hours) | | | | | | |
|---|---|---|---|---|---|---|---|---|
| | | 0 | 0.03 | 0.25 | 0.5 | 1 | 4 | 24 |
| | 16 | 2.40E+05 | 2.08E+05 | 2.26E+05 | 1.32E+05 | 1.00E+03 | <2.00E+02 | <2.00E+02 |
| | 64 | 2.40E+05 | 3.20E+04 | 1.16E+04 | 7.40E+03 | 6.00E+02 | <2.00E+02 | <2.00E+02 |
| | 256 | 2.40E+05 | 1.96E+04 | 1.20E+03 | <2.00E+02 | <2.00E+02 | <2.00E+02 | <2.00E+02 |

For *S. aureus* ATCC 29213 the time kill kinetics for C-101 and E-101 were similar. Bactericidal activity (defined as a >3 $\log_{10}$ decrease in CFU's/ml compared to the starting inoculum) was achieved within four hours regardless of the concentrations of C-101 or E-101 tested.

For *E. faecalis* ATCC 29212 C-101 and E-101 bactericidal activity within four hours was achieved only at concentrations of 16, 64, and 256 µg/ml. Cidality was not achieved at 24 hours for either formulation at concentrations of 0.06 and 0.25 µg/ml, respectively (Tables 3 and 4). Cidality was achieved at 24 hours at concentrations of 1 and 4 µg/ml for both formulations.

For *E. coli* ATCC 29212 bactericidal activity was achieved by each formulation at every concentration tested except 0.06 µg/ml. At this lowest concentration neither formulation achieved cidality even after 24 hours (Tables 3 and 4).

For *P. aeruginosa* ATCC 27853 both C-101 and E-101 were bactericidal by four hours at every concentration tested.

As determined by the time kill kinetic study, C-101 and E-101 exhibited very similar bactericidal activities against the four organisms tested.

While the preferred embodiment of the invention has been illustrated and described, it will be appreciated that various changes can be made therein without departing from the spirit and scope of the invention.

The invention claimed is:

1. A composition for killing or inhibiting the growth of non-sporular bacteria, comprising:
   (a) an eosinophil peroxidase;
   (b) glucose oxidase; and
   (c) amino acids glycine, L-alanine, and L-proline, wherein the amino acids enhance the antibacterial activity of the eosinophil peroxidase.

2. The composition of claim 1, further comprising a bromide.

3. The composition of claim 1, comprising from about 0.1 to about 1,000 µg/ml of eosinophil peroxidase.

4. The composition of claim 1, comprising from about 0.1 to about 500 mM of each amino acid.

5. The composition of claim 1, comprising from about 1 to about 500 U/ml of glucose oxidase.

6. A method for killing or inhibiting the growth of non-sporular bacteria comprising, contacting the non-sporular bacteria with an effective amount of a composition of claim 1.

7. A method of treating a non-sporular bacterial infection in a human or animal subject, comprising administering to the site of infection an effective amount of a composition of claim 1.

8. A method of treating a non-sporular bacterial infection of a surgical site in a human or animal subject, comprising administering to the surgical site an effective amount of a composition of claim 1.

9. The method of claim 8, wherein the surgical site is a cancer surgical site.

10. The method of claim 9, wherein the cancer surgical site is a colorectal cancer surgical site.

11. The method of claim 9, wherein the cancer surgical site is a brain cancer surgical site.

12. The method of claim 8, wherein the surgical site is a laparoscopic surgical site.

13. The method of claim 7, wherein the non-sporular bacterial infection is a multidrug resistant infection.

14. A binary combination for killing or inhibiting the growth of non-sporular bacteria, comprising:
   (a) a first composition comprising an eosinophil peroxidase; glucose oxidase; and amino acids glycine, L-alanine, and L-proline, wherein the amino acids enhance the antibacterial activity of the eosinophil peroxidase; and
   (b) a second composition comprising glucose,
   wherein the binary combination is effective for killing or inhibiting the growth of non-sporular bacteria when the first composition and the second composition are combined in a single solution and come in contact with the non-sporular bacteria.

15. The binary combination of claim 14, wherein the first composition, the second composition, or both the first composition and the second composition further comprise a bromide.

16. A binary combination for killing or inhibiting the growth of non-sporular bacteria, comprising:
   (a) a first composition comprising an eosinophil peroxidase; glucose oxidase; and amino acids glycine, L-alanine, and L-proline, wherein the amino acids enhance the antibacterial activity of the eosinophil peroxidase; and
   (b) a second composition comprising glucose,
   wherein the binary combination is effective for killing or inhibiting the growth of non-sporular bacteria when the first composition and the second composition are each in solution form and are applied concurrently to the non-sporular bacteria.

17. A binary combination for killing or inhibiting the growth of non-sporular bacteria, comprising:
   (a) a first composition comprising an eosinophil peroxidase; glucose oxidase; and amino acids glycine, L-alanine, and L-proline, wherein the amino acids enhance the antibacterial activity of the eosinophil peroxidase; and
   (b) a second composition comprising glucose,
   wherein the binary combination is effective for killing or inhibiting the growth of non-sporular bacteria when the first composition and the second composition are each in solution form and are applied sequentially to the non-sporular bacteria.

* * * * *